United States Patent
Xiao et al.

(10) Patent No.: US 10,687,960 B2
(45) Date of Patent: Jun. 23, 2020

(54) ASSEMBLED VERTEBRAL BODY

(71) Applicant: SECOND AFFILIATED HOSPITAL OF SECOND MILITARY MEDICAL UNIVERSITY, SHANGHAI, Shanghai (CN)

(72) Inventors: Jianru Xiao, Shanghai (CN); Xinghai Yang, Shanghai (CN); Haiyi Gong, Shanghai (CN); Dan Zhang, Shanghai (CN); Wei Xu, Shanghai (CN); Zhipeng Wu, Shanghai (CN); Jian Jiao, Shanghai (CN); Bowen Yuan, Shanghai (CN); Da Wang, Shanghai (CN); Shaohui He, Shanghai (CN)

(73) Assignee: SECOND AFFILIATED HOSPITAL OF SECOND MILITARY MEDICCAL UNIVERSITY, SHANGHAI, Shanghai (CN)

( * ) Notice: Subject to any disclaimer, the term of this patent is extended or adjusted under 35 U.S.C. 154(b) by 0 days.

(21) Appl. No.: 15/961,281

(22) Filed: Apr. 24, 2018

(65) Prior Publication Data
US 2019/0029842 A1    Jan. 31, 2019

(30) Foreign Application Priority Data

Apr. 25, 2017  (CN) ............................ 2017 1 0277172
Apr. 25, 2017  (CN) ............................ 2017 1 0277173
Feb. 8, 2018   (CN) ............................ 2018 1 0130694

(51) Int. Cl.
*A61F 2/44* (2006.01)
*A61B 17/80* (2006.01)
(Continued)

(52) U.S. Cl.
CPC .......... *A61F 2/446* (2013.01); *A61B 17/8061* (2013.01); *A61F 2/4465* (2013.01);
(Continued)

(58) Field of Classification Search
CPC ................................................. A61F 2/44–447
See application file for complete search history.

(56) References Cited

U.S. PATENT DOCUMENTS 5,192,327 A * 3/1993 Brantigan ................. A61F 2/44
606/247
5,458,641 A * 10/1995 Ramirez Jimenez ..... A61F 2/44
403/43
(Continued)

FOREIGN PATENT DOCUMENTS

CN    101843519 A    9/2010
CN    102240234 A    11/2011
(Continued)

*Primary Examiner* — Nicholas J Plionis
(74) *Attorney, Agent, or Firm* — Sinorica, LLC

(57) ABSTRACT

The invention relates to an assembled vertebral body used in a cervical reconstruction operation, comprising: an upper connecting element, an artificial vertebral body element and a lower connecting element, wherein the upper connecting element is disposed at an upper part of the artificial vertebral body element, the lower connecting element is disposed at an lower part of the artificial vertebral body element, and wherein the artificial vertebral body element is assembled with the upper connecting element and the lower connecting element, respectively. The invention has the advantages that the artificial vertebral body element is customized in accordance with the characteristics of patients and printed in 3D, and the length of the artificial vertebral body element can be precisely adjusted to adapt to the patient. Since the lower connecting element is standard part, the upper connecting element is standard part or non-standard part, and the artificial vertebral body element is non-standard part, in comparison to the traditional 3D printing which needs to be printed integrally, the adjustable assembled artificial vertebral body can reduce 3D printing materials and reduce the cost of 3D printing, thus reducing medical costs for the (Continued)

patient. The shape of the nested parts of the elements is a non-circular shape, which can resist rotation, so that no relative movement occurs among the three elements of the artificial vertebral body.

18 Claims, 23 Drawing Sheets

(51) Int. Cl.
*A61L 27/32* (2006.01)
*A61L 27/56* (2006.01)
*A61F 2/30* (2006.01)
*A61B 17/56* (2006.01)
*A61B 17/00* (2006.01)
*A61B 17/70* (2006.01)

(52) U.S. Cl.
CPC .............. *A61L 27/32* (2013.01); *A61L 27/56* (2013.01); *A61B 17/7059* (2013.01); *A61B 2017/00526* (2013.01); *A61B 2017/568* (2013.01); *A61F 2002/30112* (2013.01); *A61F 2002/30125* (2013.01); *A61F 2002/30172* (2013.01); *A61F 2002/30233* (2013.01); *A61F 2002/30354* (2013.01); *A61F 2002/30355* (2013.01); *A61F 2002/30383* (2013.01); *A61F 2002/30507* (2013.01); *A61F 2002/30578* (2013.01); *A61F 2002/30593* (2013.01); *A61F 2002/30599* (2013.01); *A61F 2002/30604* (2013.01); *A61F 2002/30622* (2013.01); *A61F 2002/30841* (2013.01); *A61F 2002/30985* (2013.01); *A61F 2310/00796* (2013.01); *A61L 2430/38* (2013.01)

(56) References Cited

U.S. PATENT DOCUMENTS

| | | | | |
|---|---|---|---|---|
| 6,086,613 | A * | 7/2000 | Camino | A61F 2/44 623/17.16 |
| 6,106,557 | A * | 8/2000 | Robioneck | A61F 2/44 606/246 |
| 6,159,211 | A * | 12/2000 | Boriani | A61F 2/44 606/247 |
| 2002/0138142 | A1* | 9/2002 | Castro | A61F 2/4465 623/17.11 |
| 2003/0191531 | A1* | 10/2003 | Berry | A61F 2/44 623/17.11 |
| 2003/0199980 | A1* | 10/2003 | Siedler | A61F 2/44 623/17.11 |
| 2004/0068318 | A1* | 4/2004 | Coates | A61F 2/44 623/17.11 |
| 2004/0193272 | A1* | 9/2004 | Zubok | A61B 17/8042 623/17.11 |
| 2005/0096744 | A1 | 5/2005 | Trieu et al. | |
| 2006/0116770 | A1 | 6/2006 | White | |
| 2009/0105835 | A1* | 4/2009 | Hovda | A61F 2/4465 623/17.16 |
| 2011/0045087 | A1* | 2/2011 | Kerr | A61N 1/3622 424/490 |
| 2013/0197642 | A1* | 8/2013 | Ernst | A61F 2/442 623/17.16 |

FOREIGN PATENT DOCUMENTS

| | | |
|---|---|---|
| CN | 102715969 A | 10/2012 |
| CN | 102860864 A | 1/2013 |
| CN | 103830024 A | 6/2014 |
| CN | 106510905 A | 3/2017 |
| GB | 2364643 A | 6/2002 |

* cited by examiner

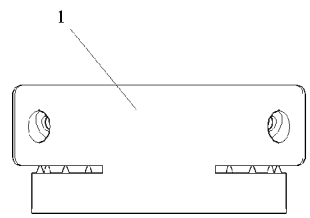
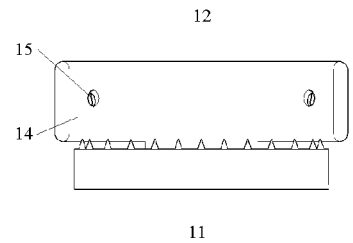
FIG. 1A   FIG. 1B
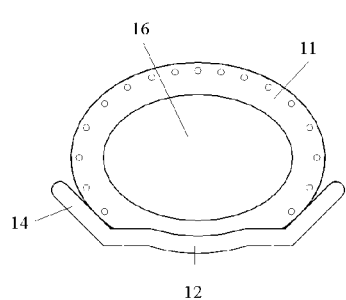
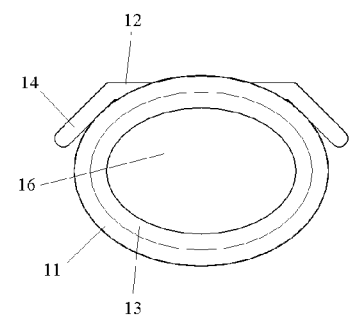
FIG. 1C   FIG. 1D
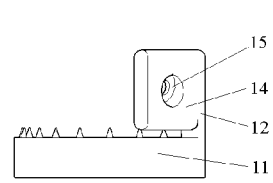
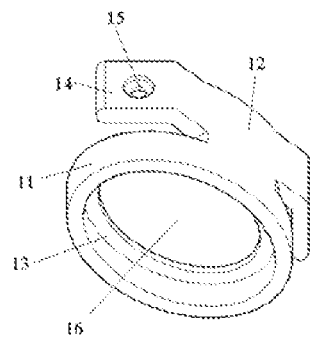
FIG. 1E   FIG. 1F

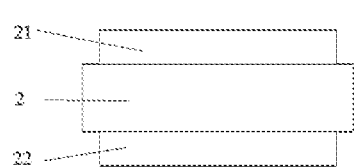
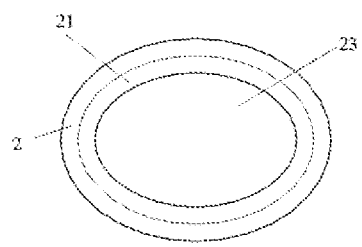
FIG. 2A  FIG. 2B
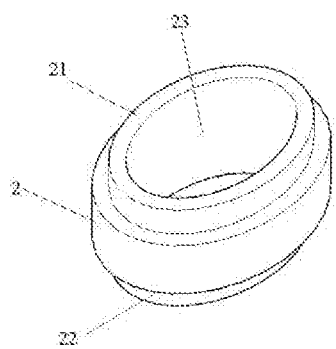
FIG. 2C

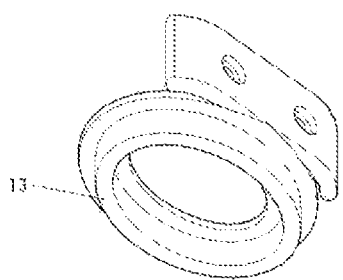
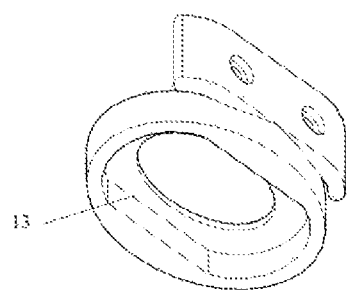
FIG. 12A  FIG. 12B
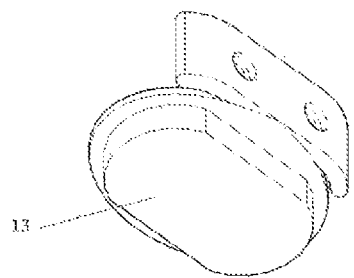
FIG. 12C

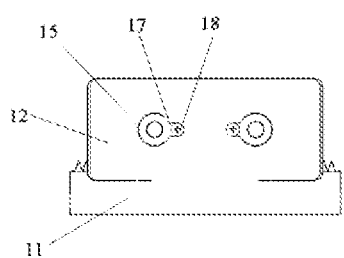
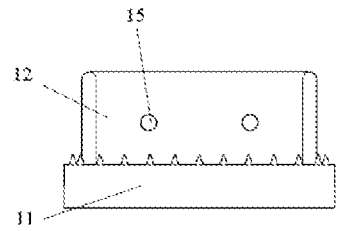
FIG. 14A  FIG. 14B
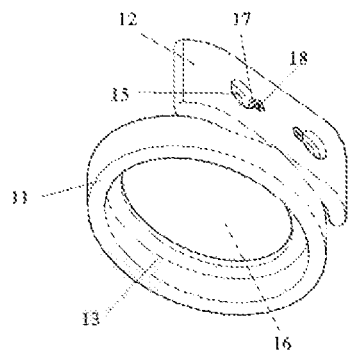
FIG. 14C

FIG. 17A                    FIG. 17B

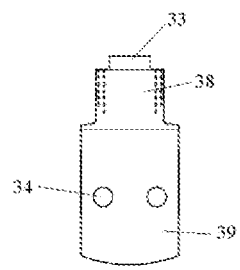
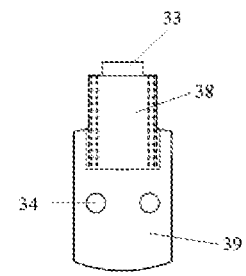
FIG. 18A　　　　　　　　　　　　FIG. 18B
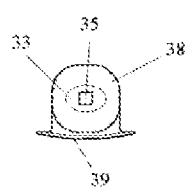
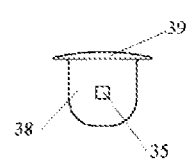
FIG. 18C　　　　　　　　　　　　FIG. 18D
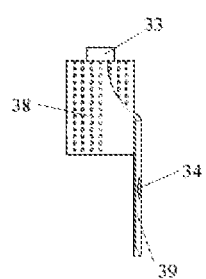
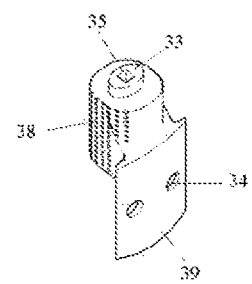
FIG. 18E　　　　　　　　　　　　FIG. 18F

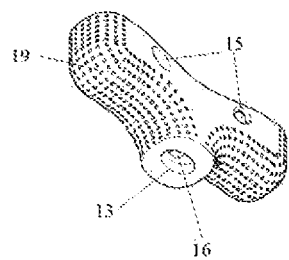
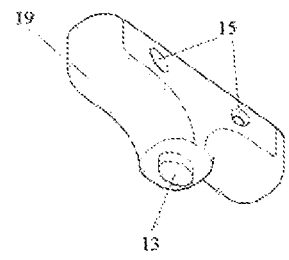
FIG. 19A  FIG. 19B
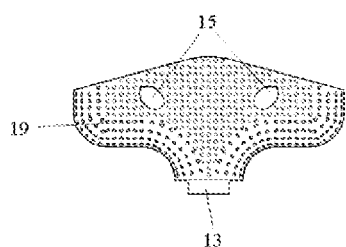
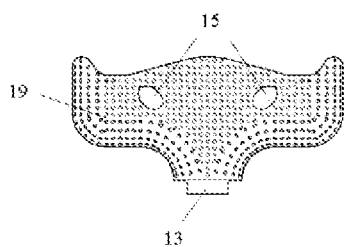
FIG. 19C  FIG. 19D

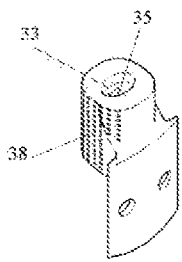
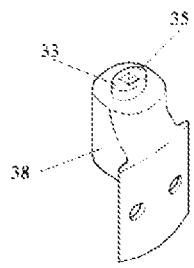
FIG. 21A  FIG. 21B
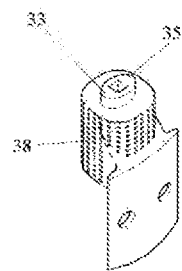
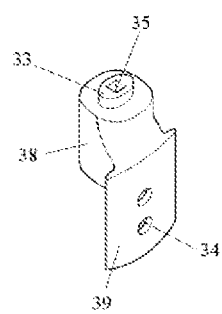
FIG. 21C  FIG. 21D
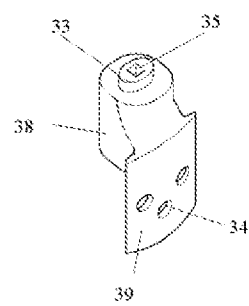
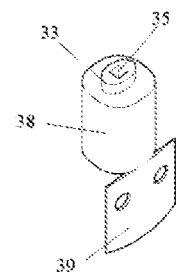
FIG. 21E  FIG. 21F

ASSEMBLED VERTEBRAL BODY

CROSS-REFERENCE TO RELATED APPLICATIONS

The present application claims priority to the benefit of Chinese Patent Application No. CN201710277172.7, filed on Apr. 25, 2017, Chinese Patent Application No. CN 201710277173.1, filed on Apr. 25, 2017 and Chinese Patent Application No. CN 201810130694.9, filed on Feb. 8, 2018, the entire content of which is incorporated herein by reference.

BACKGROUND OF THE INVENTION

1. Field of the Invention

The invention relates to the technical field of vertebral body reconstruction, and more particularly, to an assembled vertebral body.

2. Description of the Related Art

As a type of effective vertebral body replacement, an artificial vertebral body is widely used in clinic. It has brought great convenience for the treatment of diseases such as spinal tumors. The artificial vertebral body can not only play a role in restoration of physiological anatomy of the spine and correction of kyphosis of the spine, but also have achieved a great success in reconstruction of the spine stability.

With the development of vertebral body reconstruction and fusion technology, the artificial vertebral body, as a vertebral body replacement, provides doctors and patients with more treatment options. However, the traditional artificial vertebral body still has some defects in the treatment, for example, the connection between an upper and a lower vertebral body is not reliable, resulting in vertebral body prolapse, and therefore, satisfactory bony fusion and high stability cannot be achieved.

The development of the artificial vertebral body has gone through several development stages such as simple support, distraction fixation, and adjustable fixation. However, in the prior art, since artificial vertebra body height adjustment is mainly centered on spiral adjustment, it cannot be fixed and reliability is not high after being adjusted. The adjustment angle is obtained through an inherent angle between an upper endplate and a lower endplate of the artificial vertebral body, therefore, the adjustment range is limited, and it is difficult to fully achieve the purpose of restoring the physiological curvature. Moreover, since the artificial vertebral body itself and the adjacent vertebral body are not effectively fixed, the fixation strength can only be reinforced by an auxiliary fixed nail rod or nail plate.

The human cervical spine is composed of seven vertebrae, of which the two uppermost vertebraes which are connected with the base of the skull are the atlas and the axis, respectively. When it is observed between the atlantoaxial and human skull, the relative position between them is similar to a ball being placed on a triangular tip, which enables the skull to make movements such as flexion and extension, left and right lateral flexion, and left and right rotations, and a ring rotation movement formed by the above-mentioned movements, but unfortunately, it makes the atlantoaxial become the most unstable and most vulnerable fulcrum in the cervical spine. In addition, there is a maximal arterial branch, the vertebral artery, which supplies blood to the base of the brain.

Many tumors in the cervical spinal tumors relate to the vertebral body. When the tumor is being removed, the diseased vertebral body needs to be removed as well. After the lesion segment of the vertebral body is removed, reconstruction of the internal fixation is required to achieve the support.

However, during the reconstruction of the vertebral body, the reconstruction is usually done by using a titanium mesh plus titanium plate. The titanium mesh is placed in the surgical resection region, and the titanium plate is placed in front of the titanium mesh, and the titanium mesh and the titanium plate are fixed on the adjacent vertebral bodies above the surgical resection region, and screws are used for nailing operation. This kind of reconstruction method can only be used to reconstruct the cervical spine below the axis, and the titanium mesh has a small contact surface and is prone to long-term complications such as subsidence and displacement.

The Chinese invention patent CN201010177111.1 discloses a dynamic cervical vertebra internal fixing device. The device comprises an artificial cervical vertebra body and an artificial intervertebral disc. The artificial intervertebral disc comprises artificial nucleus pulposus and an artificial end plate which are connected in sequence. The artificial intervertebral disc is fixed on the upper side and the lower side of the artificial cervical vertebral body, and the artificial vertebral body and the adjacent vertebra body are fixedly connected by using a screw. Performing fixation at operative levels on patients to whom the anterior approach for cervical spine subtotal cervical corpectomy is applicable. The stability and mobility of the cervical spine are retained, and dynamic fixation is achieved. However, this type of vertebral body is fixed in size and cannot be customized according to different patients. Although it is also an assembled artificial vertebral body, this kind of assembly that is connected by screws is prone to slippage and causes secondary injury.

The Chinese invention patent 201110179966.2 discloses an adjustable artificial cervical vertebra and intervertebral connecting complex. The adjustable artificial cervical vertebra and intervertebral connecting complex comprises a centrum part and two end plate parts, wherein the two end plate parts are connected with the upper section and the lower section of the centrum part respectively through fetlock structures; the centrum part comprises an upper centrum part and a lower centrum part, and the upper centrum part and the lower centrum part can be adjusted in length and fixed together by means of a bolt with fixed length. The artificial centrum has the supporting function of the artificial centrum and the movability of the artificial intervertebral disk, is adjustable in length, can realize immediate stability and supporting function. However, due to the use of screws to fix the upper and lower centrum and to adjust the length, the screws will easily fall off, and the upper and lower centrum displacement occurs, causing damage to the cervical spine.

The Chinese invention patent CN201210395040.1 discloses a second cervical vertebra displacer having a fusion structure, comprising an atlas connecting part, a fixed connecting part and a third cervical vertebra connecting part, wherein the atlas connecting part is fixedly connected with the atlas through screws. The displacer makes an interbody fusion cage screw and a vertebra body be fused integrally, and the connecting performance and the fixing performance of the displacer are improved, and the length of the displacer can be regulated as required. However, in this invention, the first cervical vertebra and the third cervical vertebra are fused together through the displacer to become a vertebral body, such that the flexibility of the vertebral body is reduced.

The Chinese invention patent CN201210232087.6 discloses a discloses a combined artificial vertebral body, comprising a convex cover plate, a concave cover plate, a fixing bolt, an inner support block, an outer support block and a spring, wherein the inner support block is installed in an inner bore of the outer support block, and the spring is inserted into the inner bore of the inner support block, and the concave cover plate is installed at both ends of the outer support block by fixing bolts, and the two convex cover plates are assembled to the concave spherical surface of the two concave cover plates through the convex ball, so as to form the artificial vertebral body. Complications, such as degeneration caused by excessive bearing capacity of a single vertebral body, are avoided through axial mobility of the artificial vertebral body, such that force can be distributed evenly in each vertebral body and the artificial vertebral body. In addition, the artificial vertebral body with a concavo-convex spherical surface guarantee the possibility of an axial rotation between the normal body and the artificial vertebral body, so that the lesion site still maintain a certain degree of rotational activity. However, since the combined artificial vertebral body is a standard part, that is, it cannot be customized for each patient. Since the height of the vertebral body removed from the patient is not uniform, the vertebral body cannot be closely fitted to the upper and lower vertebral bodies, and the artificial vertebral body can easily fall off due to the absence of a corresponding fixture after the insertion of the artificial vertebral body.

The Chinese invention patent CN201410078312.4 discloses an adjustable angle and height telescopic artificial vertebral body. The vertebral body comprises a top fixing plate, a bottom fixing plate, an upper vertebral element, a lower vertebral element and screws. A first joint and angle adjustment mechanism is disposed between the top fixing plate and the upper vertebral element, a second joint and angle adjustment mechanism is disposed between the bottom fixing plate and the lower vertebral element, and a vertically telescopic adjustment mechanism is disposed between the upper vertebral element and the lower vertebral element. The artificial vertebral body has the advantages that the angle and the height of the artificial vertebral body can be adjusted conveniently and quickly, and operation time can be shortened and patients bear fewer wounds.

The Chinese invention patent CN201611038312.7 discloses an artificial vertebral body whose self-stability can be adjusted. The vertebral body comprises an upper vertebral body, a lower vertebral body and a locking member, wherein the upper vertebral body is interposed into the lower vertebral body. A limit stop is arranged between the upper vertebral body and the lower vertebral body, and the upper vertebral body can be adjusted in an axial direction. The artificial vertebral body can be adjusted according to the requirements of different vertebral heights to satisfy the operations for total resection of a single and multiple vertebral bodies. However, this type of artificial vertebral body still has the defects that the upper vertebral body and the lower vertebral body cannot be fixed together due to the detachment of locking pieces, and thus to make patients suffer from postoperative pain.

Therefore, it is in urgent need of an assembled vertebral body adapted to different patients and to different vertebral body resections, which can reduce postoperative pain and contribute to postoperative spinal stability for patients. The artificial vertebral body is firmly attached to the upper and lower vertebral body, and there is no axial rotation of the assembled vertebral body.

SUMMARY OF THE INVENTION

Aiming at the defects in the prior art, the present invention provides an assembled vertebral body.

In order to achieve the abovementioned purposes, the invention adopts the following technical solution.

An assembled vertebral body used in a cervical reconstruction operation, comprising: an upper connecting element, an artificial vertebral body element and a lower connecting element, wherein the upper connecting element is disposed at an upper part of the artificial vertebral body element, the lower connecting element is disposed at an lower part of the artificial vertebral body element, and wherein the artificial vertebral body element is assembled with the upper connecting element and the lower connecting element, respectively.

Preferably, wherein the artificial vertebral body element is nestedly connected with the upper connecting element and the lower connecting element, respectively.

Preferably, wherein the upper connecting element comprises a first nesting part disposed at a lower part of the upper connecting element; the lower connecting element comprises a second nesting part disposed at an upper part of the lower connecting element; and the artificial vertebral body element comprises a third nesting part disposed at the upper part of the artificial vertebral body element, and a fourth nesting part disposed at the lower part of the artificial vertebral body element; and wherein the first nesting part is nestedly connected with the third nesting part, and the second nesting part is nestedly connected with the fourth nesting part.

Preferably, wherein the first nesting part and the second nesting part are protruding blocks, the third nesting part and the fourth nesting part are recessed grooves.

Preferably, the first nesting part and the fourth nesting part are the protruding blocks, and the second nesting part and the third nesting part are recessed grooves.

Preferably, the first nesting part and the fourth nesting part are recessed grooves, and the second nesting part and the third nesting part are protruding blocks;

Preferably, the first nesting part and the second nesting part are recessed grooves, and the third nesting part and the fourth nesting part are protruding blocks.

Preferably, wherein the nested connection is an anti-axial rotation nested connection.

Preferably, wherein the first nesting part, the second nesting part, the third nesting part and the fourth nesting part have a non-circular shape.

Preferably, wherein the non-circular shape is an ellipse or a rounded rectangle.

Preferably, wherein the upper connecting member further comprises a coupling plate and a fixing plate, and wherein the fixing plate is disposed at an upper part of the coupling plate, and the first nesting part is disposed at a lower part of the coupling plate.

Preferably, wherein the fixing plate is T-shaped.

Preferably, wherein two fixed wings, bent inward at a certain angle, are provided at a left and a right side of the fixing plate, respectively.

Preferably, the fixed wings are bent inward at an angle of 0°-90°.

Preferably, wherein the fixing plate comprises nail holes symmetrically disposed throughout the fixed wings on both sides of the fixing plate.

Preferably, wherein the nail holes penetrate upwardly from an outer side of the fixed wing to an inner side of the fixed wing at an angle with respect to a horizontal plane.

Preferably, wherein the nail holes penetrate upwardly from an outer side of the fixed wing to an inner side of the fixed wing at an angle of 0°-90° with respect to a horizontal plane.

Preferably, wherein the fixing plate is straight line-shaped.

Preferably, wherein the fixing plate comprises nail holes symmetrically disposed throughout a left side and a right side of the fixing plate.

Preferably, wherein the upper connecting element comprises a locking device disposed around the nail hole.

Preferably, wherein the locking device comprises a locking slot disposed on one side of the nail hole and a locking screw disposed within the locking slot.

Preferably, wherein the lower connecting element further comprises a coupling plate and a fixing plate, and wherein the fixing plate is disposed at the lower part of the coupling plate, and the second nesting part is disposed at the upper part of the coupling plate.

Preferably, wherein the fixing plate is straight line-shaped.

Preferably, wherein the fixing plate comprises nail holes symmetrically disposed throughout the left side and the right side of the fixing plate.

Preferably, wherein the lower connecting element comprises a locking device disposed around the nail hole.

Preferably, wherein the locking device comprises a locking slot disposed on one side of the nail hole and a locking screw disposed within the locking slot.

Preferably, wherein the upper connecting element further comprises a transverse portion, and the first nesting part is disposed at a lower part of the transverse portion.

Preferably, wherein the transverse portion comprises nail holes symmetrically disposed on a left and a right side of a front end surface of the transverse portion, and the nail holes penetrate the front end surface of the transverse portion and an upper end surface of the transverse portion.

Preferably, wherein the transverse portion is straight line-shaped;

Preferably, the transverse portion is V-shaped or has a shape of a semi-concave sphere, and a left and a right end of the transverse portion project upwards.

Preferably, the transverse portion is inverted V-shaped or has the shape of a semi-convex sphere, and the left and the right end of the transverse portion project downwards.

Preferably, the transverse portion is W-shaped, and the left end, the right end and a central portion of the transverse portion project upwards.

Preferably, wherein the lower connecting element further comprises a transition portion and a mating portion, wherein the mating portion is disposed at a lower portion of the transition portion, and the second nesting part is disposed at an upper portion of the transition portion.

Preferably, wherein the mating portion comprises nail holes penetrating a front end surface and a rear end surface of the mating portion.

Preferably, wherein two nail holes are provided, and the nail holes are symmetrically and horizontally arranged.

Preferably, wherein two nail holes are provided, and the nail holes are symmetrically and vertically arranged.

Preferably, wherein three nail holes are provided, the nail holes are symmetrically arranged in a triangle.

Preferably, wherein an upper surface of the upper connecting element is provided with a small-tooth structure.

Preferably, a lower surface of the lower connecting element is provided with a small-tooth structure.

Preferably, wherein the upper connecting element is a hollow structure.

Preferably, wherein the hollow structure is a bone graft channel, and the bone graft channel is disposed in the middle portion of the upper connecting element, and penetrates the upper end surface of the upper connecting element and the lower end surface of the upper connecting element.

Preferably, the artificial vertebral body element is a hollow structure.

Preferably, wherein the hollow structure is a bone graft channel, and the bone graft channel is disposed in the middle portion of the artificial vertebral body element, and penetrates the upper end surface of the artificial vertebral body element and the lower end surface of the artificial vertebral body element.

Preferably, wherein the lower connecting element is a hollow structure.

Preferably, wherein the hollow structure is a bone graft channel, and the bone graft channel is disposed in the middle portion of the lower connecting element, and penetrates the upper end surface of the lower connecting element and the lower end surface of the lower connecting element.

Preferably, the upper connecting element is a solid structure.

Preferably, the artificial vertebral body element is a solid structure.

Preferably, the lower connecting element is a solid structure.

Preferably, wherein the upper surface of the upper connecting element and the lower surface of the lower connecting element are provided with a biological hydroxyapatite coating.

Preferably, the biological hydroxyapatite coating is applied using a plasma oxidation technique.

Preferably, wherein a surface of the upper connecting element is a polished structure.

Preferably, wherein a surface of the artificial vertebral body element is a polished structure.

Preferably, wherein a surface of the lower connecting element is a polished structure.

Preferably, wherein spongey microporous structure are distributed on the surface of the upper connecting element.

Preferably, wherein spongy microporous structure are distributed on the surface of the artificial vertebral body element.

Preferably, wherein spongy microporous structure are distributed on the surface of the lower connecting element.

Preferably, wherein a front end surface and/or a rear end surface of the upper connecting element is a polished structure, and the rest of surfaces are distributed with the spongy microporous structure.

Preferably, the front end surface and/or the rear end surface of the artificial vertebral body element is a polished structure, and the rest of the surfaces are distributed with the spongy microporous structure;

Preferably, the front end surface and/or the rear end surface of the lower connecting element is the polished structure, and the rest of the surfaces are distributed with the spongy microporous structure.

By adopting the above technical solution, the present invention has the following technical effects over the prior art:

In the assembled vertebral body of the invention, the artificial vertebral body element is customized in accordance with the characteristics of patients and printed in 3D, and the length of the artificial vertebral body element can be precisely adjusted to adapt to the patient. It is known that 3D printing for an integral part of the artificial vertebral body is required in previous days, while since the lower connecting element is standard part, the upper connecting element is standard part or non-standard part, and the artificial vertebral body element is non-standard part, the adjustable and assembled artificial vertebral body can reduce 3D printing materials and reduce the cost of 3D printing, thus reducing medical costs for the patient. The shape of the nested parts of the elements is a non-circular shape, which can resist rotation, so that no relative movement occurs among the three elements of the artificial vertebral body, which reduces postoperative pain and enhances the stability of the cervical vertebra. The upper cervical vertebra reconstruction prosthesis is able to perform occipitocervical reconstruction after atlantoaxial resection by means of load-bearing fixing, which solves the problem that the traditional reconstruction method can only perform reconstruction of the cervical vertebra below the axis. The contact area between the upper end of the reconstruction prosthesis and the anterior arch of the atlas or skull base is large, which helps to form an effective support, and is conducive to bone ingrowth, and thus to avoid long-term complications such subsidence and shift of the prosthesis due to the small contact area of the traditional titanium mesh. Prosthesis surface comprises spongy microporous structure facilitating the fusion of the prosthesis and the adjacent bones. The bone graft channel is arranged in the center of the prosthesis, and the inner diameter of the bone graft channel can be designed according to the needs of the operation, which facilitates the filling of a sufficient amount of allograft bone for ease of bone implantation, achieving fusion. The prosthesis shape is designed according to the patient's imaging measurements, such that the prosthesis can well fit the atlas, and it is in accordance with the physiological structure and biomechanical characteristics of the atlanto-axial joint, thus achieving an accurate match to make the reconstruction more stable. The upper end of the prosthesis is fixed to the lateral mass of the atlas through obliquely upward screws, and the lower end of the prosthesis is cross-fixed through vertebral screws and endplate screws, which is resistant to pull-out and rotation. The screw hole angle at the upper end of the prosthesis is designed according to the results of the patient's imaging measurements, such that the maximum height of the upper end of the prosthesis can be fixed with the occipital condyle of the skull base, which overcomes the problem that the traditional prosthesis can only achieve the reconstruction below the axis. This design can achieve the reconstruction of the prosthesis after the atlas resection.

BRIEF DESCRIPTION OF THE DRAWINGS

The accompanying drawings, together with the specification, illustrate exemplary embodiments of the present disclosure, and, together with the description, serve to explain the principles of the present invention.

FIG. 1A is a front view of the upper connecting element of a first preferred embodiment of the present invention;

FIG. 1B is a rear view of the upper connecting element;

FIG. 1C is a top view of the upper connecting element;

FIG. 1D is a bottom view of the upper connecting element;

FIG. 1E is a side view of the upper connecting element;

FIG. 1F is a perspective view of the upper connecting element.

FIG. 2A is a front view of the artificial vertebral body element of the first preferred embodiment of the present invention;

FIG. 2B is a top view (bottom view) of the artificial vertebral body element;

FIG. 2C is a perspective view of the artificial vertebral body element.

FIG. 12A is a schematic view of a first alternative embodiment of the upper connecting element of the third preferred embodiment of the present invention;

FIG. 12B is a schematic view of a second alternative embodiment of the upper connecting element;

FIG. 12C is a schematic view of a third alternative embodiment of the upper connecting element.

FIG. 14A is a front view of the upper connecting element of a fourth preferred embodiment of the present invention;

FIG. 14B is a rear view of the upper connecting element;

FIG. 14C is a perspective view of the upper connecting element.

FIG. 17A is a front view of the artificial vertebral body element of the fifth preferred embodiment of the present invention;

FIG. 17B is a top view (bottom view) of the artificial vertebral body element;

FIG. 18A is a front view of the lower connecting element of the fifth preferred embodiment of the present invention;

FIG. 18B is a rear view of the lower connecting element;

FIG. 18C is a top view of the lower connecting element;

FIG. 18D is a bottom view of the lower connecting element;

FIG. 18E is a side view of the lower connecting element; and

FIG. 18F is a perspective view of the lower connecting element.

FIG. 19A is a schematic view of a first alternative embodiment of the upper connecting element of the fifth preferred embodiment of the present invention;

FIG. 19B is a schematic view of a second alternative embodiment of the upper connecting element;

FIG. 19C is a schematic view of a third alternative embodiment of the upper connecting element;

FIG. 19D is a schematic view of a fourth alternative embodiment of the upper connecting element.

FIG. 21A is a schematic view of a first alternative embodiment of the lower connecting element of the fifth preferred embodiment of the present invention;

FIG. 21B is a schematic view of a second alternative embodiment of the lower connecting element of the fifth preferred embodiment of the present invention;

FIG. 21C is a schematic view of a third alternative embodiment of the lower connecting element of the fifth preferred embodiment of the present invention;

FIG. 21D is a schematic view of a fourth alternative embodiment of the lower connecting element of the fifth preferred embodiment of the present invention;

FIG. 21E is a schematic view of a fifth alternative embodiment of the lower connecting element of the fifth preferred embodiment of the present invention;

FIG. 21F is a schematic view of a sixth alternative embodiment of the lower connecting element of the fifth preferred embodiment of the present invention.

Figure 3A:
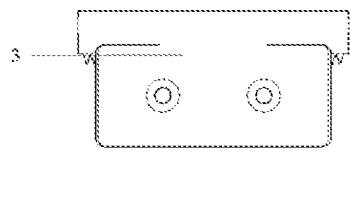
FIG. 3A is a front view of the lower connecting element of the first preferred embodiment of the present invention.

LIST OF REFERENCE NUMERALS upper connecting element 1, artificial vertebral body element 2, lower connecting element 3, coupling plate 11, fixing plate 12, first nesting part 13, fixed wing 14, nail hole 15, bone graft channel 16, locking slot 17, locking screw 18, transverse portion 19, third nesting part 21, fourth nesting part 22, bone graft channel 23, coupling plate 31, fixing plate 32, second nesting part 33, nail hole 34, bone graft channel 35, locking slot 36, locking screw 37, transition portion 38; mating portion 39.

DETAILED DESCRIPTION

The present invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the term "plurality" means a number greater than one.

Hereinafter, certain exemplary embodiments according to the present disclosure will be described with reference to the accompanying drawings.

An assembled vertebral body of the present invention, used in a vertebral body reconstruction operation, comprising: an upper connecting element, an artificial vertebral body element and a lower connecting element, wherein the upper connecting element is detachably disposed at an upper part of the artificial vertebral body element, the lower connecting element is detachably disposed at an lower part of the artificial vertebral body element.

When the artificial vertebral body element is assembled with the upper connecting element and the lower connecting element, respectively, these elements can be assembled by a plurality of assembling methods, such as by bolting and nesting.

In the present invention, the preferred assembling method is a nested connection.

In order to facilitate the assembly of the upper connecting element, the artificial vertebral body element and the lower connecting element, each element comprises a part for nesting.

The upper connecting element comprises a first nesting part disposed at a lower part of the upper connecting element.

The lower connecting element comprises a second nesting part disposed at an upper part of the lower connecting element.

The artificial vertebral body element comprises a third nesting part disposed at the upper part of the artificial vertebral body element, and a fourth nesting part disposed at the lower part of the artificial vertebral body element.

When the artificial vertebral body element is assembled with the upper connecting element and the lower connecting element, respectively, the first nesting part of the upper connecting element is nestedly connected with the third nesting part of the artificial vertebral body element, and the second nesting part of the lower connecting element is nestedly connected with the fourth nesting part of the artificial vertebral body element.

There are two nesting parts nestedly connected within each other, one of which is a protruding nesting part and the other is a recessed nesting part.

Accordingly, the following four methods of nested connections can be obtained:

1. The first nesting part of the upper connecting element is a protruding block, the second nesting part of the lower connecting element is the protruding block, and the third nesting part and the fourth nesting part of the artificial vertebral body element are recessed grooves.

2. The first nesting part of the upper connecting element is a recessed groove, the second nesting part of the lower connecting element is a recessed groove, and the third nesting part and the fourth nesting part of the artificial vertebral body element are protruding blocks.

3. The first nesting part of the upper connecting element is a protruding block, the second nesting part of the lower connecting element is a recessed groove, and the third nesting part of the artificial vertebral body element is a recessed groove, and the fourth nesting part of the artificial vertebral body element is a protruding block.

4. The first nesting part of the upper connecting element is a recessed groove, the second nesting part of the lower connecting element is a protruding block, and the third nesting part of the artificial vertebral body element is a protruding block, and the fourth nesting part of the artificial vertebral body element is a recessed groove.

It is convenient to switch among 4 nested connections through the above different nesting methods, for example, it is possible to switch the method from 1 to 3 or 4, and from 2 to 3 or 4, and vice versa, which greatly improves the versatility of the parts.

In the vertebral body reconstruction operation, in order to prevent axial rotation of the vertebral body after the operation, the shape of the nesting parts of each element is a non-circular shape, and the non-circular shape can effectively prevent the axial rotation of each element.

After being tested and optimized, in the present invention, the shape of each nesting part is an ellipse or a rounded rectangle. The above two shapes can reduce the complexity of making vertebral bodies and facilitate rapid and large-scale production.

The present invention will be described in detail with reference to the following embodiments.

Embodiment 1

In a preferred embodiment of the present invention, an assembled vertebral body comprises an upper connecting element 1, an artificial vertebral body element 2 and a lower connecting element 3.

As shown in FIG. 1A-1F, FIG. 1A is a front view of the upper connecting element 1; FIG. 1B is a rear view of the upper connecting element 1; FIG. 1C is a top view of the upper connecting element 1; FIG. 1D is a bottom view of the upper connecting element 1; FIG. 1E is a side view of the upper connecting element 1; and FIG. 1F is a perspective view of the upper connecting element 1. The upper connecting element 1 comprises a coupling plate 11, a fixing plate 12, and a first nesting part 13, wherein the fixing plate 12 is disposed at an upper part of the coupling to plate 11, and the first nesting part 13 is disposed at a lower part of the coupling plate 11.

The coupling plate 11 has an elliptical shape, and an upper surface thereof is coated with a layer of biological hydroxyapatite coating using a plasma oxidation technique and is distributed with a small-tooth structure The coupling plate 11 may be a hollow structure or a solid structure.

In this embodiment, the coupling plate 11 is a hollow structure. The hollow structure is a bone graft channel 16, and the bone graft channel is disposed in a middle of the coupling plate 11, such that bones coming into contact with the coupling plate may grow into the bone graft channel 16.

The fixing plate 12 is arranged on one side of an upper surface of the coupling plate 11. The fixing plate 12 is T-shaped. As shown in FIG. 1A, the upper connecting element 1 is I-shaped. As shown in FIG. 1E, the upper connecting element 1 is]-shaped.

Two fixed wings 14, bent inward at a certain angle, are provided at a left and a right side of the fixing plate 12, respectively. Nail holes 15 are symmetrically disposed throughout a left and a right side of the fixing wings 14, and the nail holes 15 penetrate upwardly through the fixed wings 14 from an outer side of the fixing plate 12 to an inner side of the fixing plate 12 at an angle with respect to a horizontal plane.

The fixed wings 14 bend inward at an angle of 00-90°, more preferably of 30°-60°, more preferably of 40°-50°, and most preferably of 45°.

The angle between each of the nail holes 15 and the horizontal plane ranges from 0° to 90°, preferably from 10° to 60°, more preferably from 20° to 50°, more preferably from 30° to 40°.

The first nesting part 13, which is in the shape of an ellipse, is a recesses groove.

As shown in FIG. 2A-2C, FIG. 2A is a front view of the artificial vertebral body element 2; FIG. 2B is a top view (bottom view) of the artificial vertebral body element 2; FIG. 2C is a perspective view of the artificial vertebral body element 2. The artificial vertebral body element 2 comprises a third nesting part 21 and a fourth nesting part 22, and both the third nesting part 21 and the fourth nesting part 22 are protruding blocks. The artificial vertebral body element 2 is cross-shaped.

The artificial vertebral body element 2 is in the shape of an ellipse, and the third nesting part 21 and the fourth nesting part 22 are also in the shape of an ellipse.

The artificial vertebral body element 2 may be a hollow structure or a solid structure.

In this embodiment, the artificial vertebral body element 2 is a hollow structure. The hollow structure is a bone graft channel 23, and the bone graft channel 23 is disposed in a middle of the artificial vertebral body element 2.

Figure 3B:
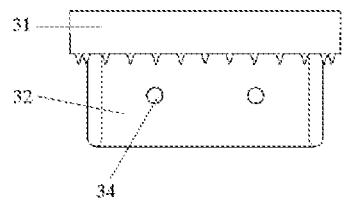
FIG. 3B is a rear view of the lower connecting element.
Figure 3C:
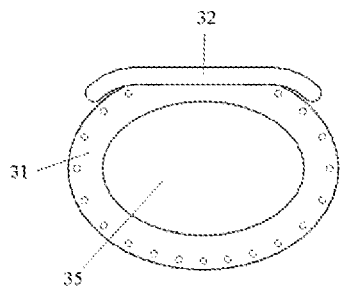
FIG. 3C is a top view of the lower connecting element.
Figure 3D:
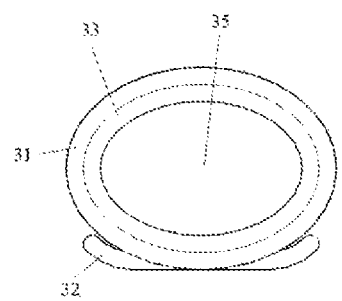
FIG. 3D is a bottom view of the lower connecting element.
Figure 3E:
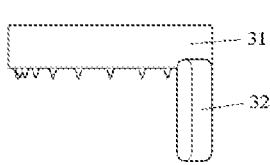
FIG. 3E is a side view of the lower connecting element.
Figure 3F:
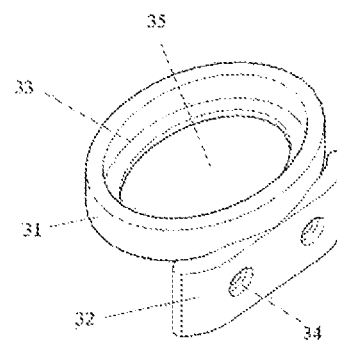
FIG. 3F is a perspective view of the lower connecting element.

As shown in FIG. 3A-3F, FIG. 3A is a front view of the lower connecting element 3; FIG. 3B is a rear view of the lower connecting element 3; FIG. 3C is a top view of the lower connecting element 3; FIG. 3D is a bottom view of the lower connecting element 3; FIG. 3E is a side view of the lower connecting element 3; and FIG. 3F is a perspective view of the lower connecting element 3. The lower connecting element 3 comprises a coupling plate 31, a fixing plate 32, and a second nesting part 33, wherein the fixing plate 32 is disposed at a lower part of the coupling plate 31, and the second nesting part 33 is disposed at an upper part of the coupling plate 31.

The coupling plate 31 has an elliptical shape, and a lower surface thereof is coated with a layer of biological hydroxyapatite coating using a plasma oxidation technique and is distributed with a small-tooth structure The coupling plate 31 may be a hollow structure or a solid structure.

In this embodiment, the coupling plate 31 is a hollow structure. The hollow structure is a bone graft channel 35, and the bone graft channel 35 is disposed in a middle of the coupling plate 31, such that bones coming into contact with the coupling plate may grow into the bone graft channel 35.

The fixing plate 32 is arranged on one side of a lower surface of the coupling plate 31. The fixing plate 31 is straight line-shaped. As shown in FIG. 3A, the lower connecting element 1 is ⊥-shaped. As shown in FIG. 3E, the lower connecting element 1 is L-shaped.

Two nail holes 34 are symmetrically and horizontally disposed at the left and right side of the fixing plate 32.

The upper connecting element 1 and the lower connecting element 3 are standard part, and the artificial vertebral body element 2 is a non-standard part. The term "standard part" means that the upper connecting element 1 and the lower connecting element 3 can be mass-produced and need not to be redesigned according to patient's health condition. The term "non-standard part" means that the artificial vertebral body element 2 needs to be designed according to the patient's health condition and made by 3D printing. Specifically, the length of the artificial vertebral body element 2 needs to be designed.

In this embodiment, the upper connecting element 1, the artificial vertebral body element 2 and the lower connecting element 3 are not limited to the above-mentioned embodiments.

Figure 4A:
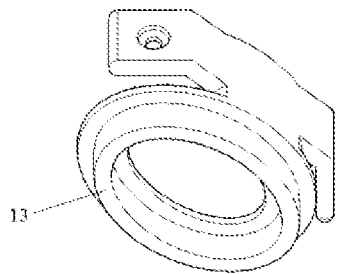
FIG. 4A is a schematic view of a first alternative embodiment of the upper connecting element of the first preferred embodiment of the present invention.
Figure 4B:
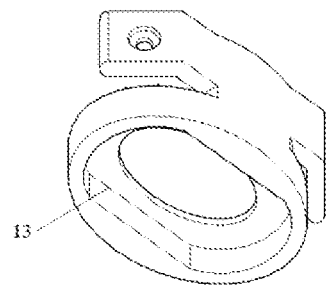
FIG. 4B is a schematic view of a second alternative embodiment of the upper connecting element.
Figure 4C:
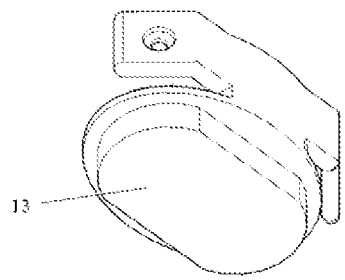
FIG. 4C is a schematic view of a third alternative embodiment of the upper connecting element.

The upper connecting element 1 of the present embodiment has following various embodiments:

Embodiment 1, as shown in FIG. 4A, the first nesting part 13 of the upper connecting element 1 is a protruding block, and the first nesting to part 13 is elliptical;

Embodiment 2, as shown in FIG. 4B, the first nesting part 13 of the upper connecting element 1 is a recessed groove, and the first nesting part 13 has a rounded rectangle shape;

Embodiment 3, as shown in FIG. 4C, the first nesting part 13 of the upper connecting element 1 is a protruding block, and the first nesting part 13 has a rounded rectangle shape. In addition, the coupling plate 11 is a solid structure without the bone graft channel 16.

Figure 5A:
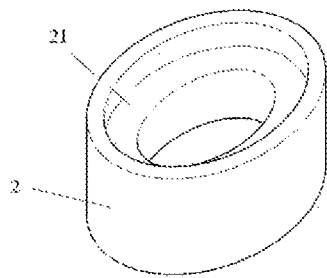
FIG. 5A is a perspective view of a first alternative embodiment of the artificial vertebral body element of the first preferred embodiment of the present invention observed from the top.
Figure 5B:
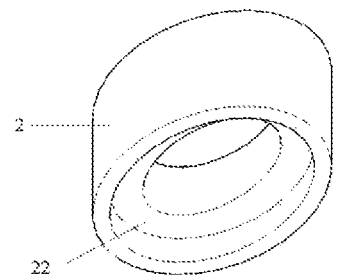
FIG. 5B is a perspective view of the first alternative embodiment of the artificial vertebral body element observed from the bottom.
Figure 5C:
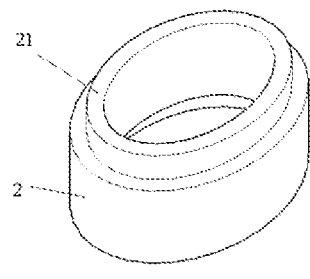
FIG. 5C is a perspective view of a second alternative embodiment of the artificial vertebral body element observed from the top.
Figure 5D:
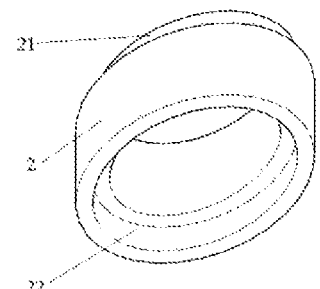
FIG. 5D is a perspective view of the second alternative embodiment of the artificial vertebral body element observed from the bottom.
Figure 5E:
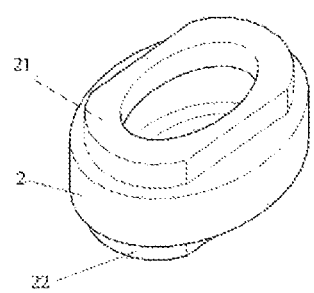
FIG. 5E is a perspective view of a third alternative embodiment of the artificial vertebral body element of the first preferred embodiment observed from the top.
Figure 5F:
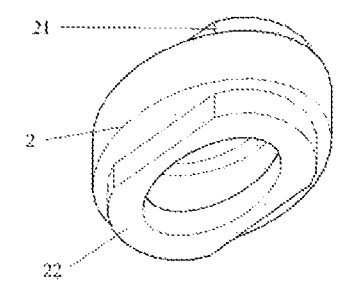
FIG. 5F is a perspective view of the third alternative embodiment of the artificial vertebral body element observed from the bottom.
Figure 5G:
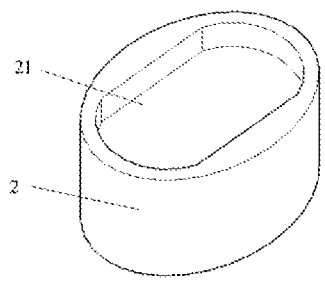
FIG. 5G is a perspective view of a fourth alternative embodiment of the artificial vertebral body element observed from the top.
Figure 5H:
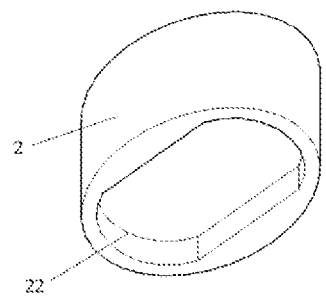
FIG. 5H is a perspective view of the fourth alternative from the top.

The artificial vertebral body element 2 of the present embodiment has following various embodiments:

Embodiment 1, as shown in FIG. 5A-5B, FIG. 5A is a perspective view of the artificial vertebral body element 2 observed from the top; FIG. 5B is a perspective view of the artificial vertebral body element 2 observed from the bottom. Both the third nesting part 21 and the fourth nesting part 22 are recessed grooves. The artificial vertebral body element 2 is H-shaped, and both the third nesting part 21 and the fourth nesting part 22 are elliptic;

Embodiment 2, as shown in FIG. 5C-5D, FIG. 5C is a perspective view of the artificial vertebral body element 2 observed from the top; FIG. 5D is a perspective view of the artificial vertebral body element 2 observed from the bottom. The third nesting part 21 of the artificial vertebral body element 2 is a protruding block, and the fourth nesting part 22 of artificial vertebral body element 2 is a recessed groove. Both the third nesting part 21 and the fourth nesting part 22 are elliptic;

Embodiment 3, as shown in FIG. 5E-5F, FIG. 5E is a perspective view of the artificial vertebral body element 2 observed from the top; FIG. 5F is a perspective view of the artificial vertebral body element 2 observed from the bottom. Both the third nesting part 21 and the fourth nesting part 22 of the artificial vertebral body element 2 are protruding blocks. The artificial vertebral body element 2 is cross-shaped, and both the third nesting part 21 and the fourth nesting part 22 have a rounded rectangle shape;

Embodiment 4, as shown in FIG. 5G-5H, FIG. 5G is a perspective view of the artificial vertebral body element 2 observed from the top; FIG. 5H is a perspective view of the artificial vertebral body element 2 observed from the bottom. Both the third nesting part 21 and the fourth nesting part 22 of the artificial vertebral body element 2 are recessed grooves. The artificial vertebral body element 2 is H-shaped, and both the third nesting part 21 and the fourth nesting part 22 have a rounded rectangle shape. In addition, the artificial vertebral body element 2 is a solid structure without the bone graft channel 23.

Figure 6A:
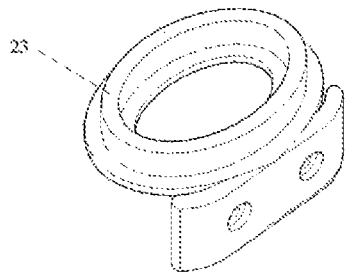
FIG. 6A is a schematic view of a first alternative embodiment of the lower connecting element of the first preferred embodiment of the present invention.
Figure 6B:
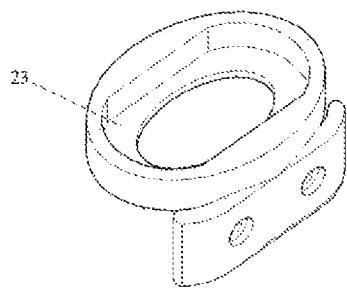
FIG. 6B is a schematic view of a second alternative embodiment of the lower connecting element.
Figure 6C:
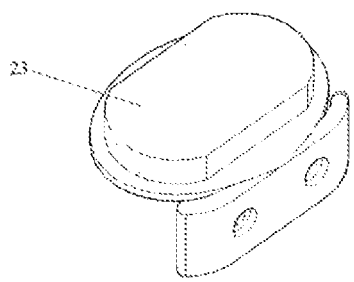
FIG. 6C is a schematic embodiment of the lower connecting element.

The lower connecting element 3 of the present embodiment has following various embodiments:

Embodiment 1, as shown in FIG. 6A, the second nesting part 33 of the lower connecting element 3 is a protruding block, and the second nesting part 33 is elliptical;

Embodiment 2, as shown in FIG. 6B, the second nesting part 33 of the lower connecting element 3 is a recesses groove, and the second nesting part 33 has a rounded rectangle shape;

Embodiment 3, as shown in FIG. 6C, the second nesting part 33 of the lower connecting element 3 is a protruding block, and the second nesting part 33 has a rounded rectangle shape. In addition, the coupling plate 31 is a solid structure without the bone graft channel 35.

Figure 7A:
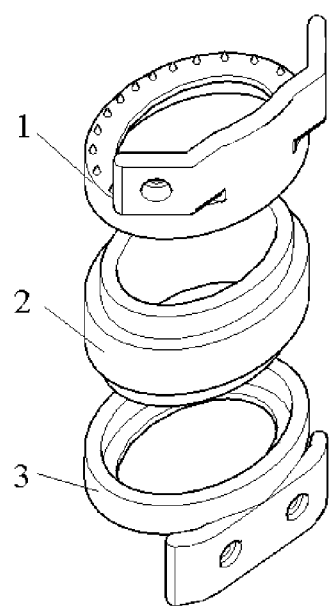
FIG. 7A is a schematic view of an assembly process in sequence of the first preferred embodiment of the present invention.
Figure 7B:
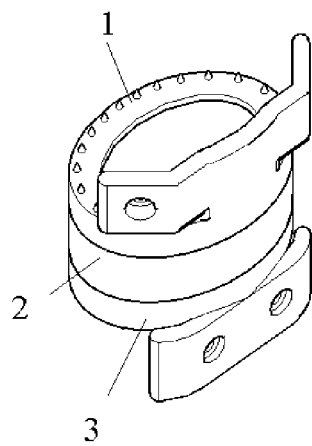
FIG. 7B is a schematic view of an assembly process in sequence of the first preferred embodiment of the present invention.
Figure 7C:
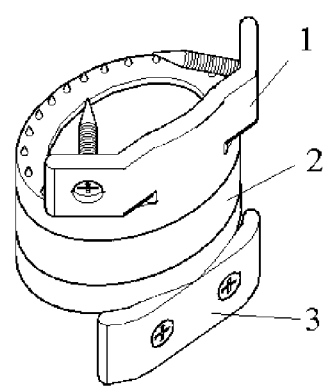
FIG. 7C is a schematic view of an assembly process in sequence of the first preferred embodiment of the present invention.

As shown in FIG. 7A-7C, the assembly process of the assembled vertebral body in this embodiment is as follows: a corresponding artificial vertebral body element 2 is designed according to the second cervical vertebrae structure of the patient and made by 3D printing; the artificial vertebral body made by 3D printing is assembled with the upper connecting element 1 and the lower connecting element 3, respectively; the assembled vertebral body is implanted into the operation site of the patient, and the upper connecting element 1 and the lower connecting element 3 are respectively fixed to the adjacent vertebral body by screws, finally, the vertebral body implantation is completed. Since the upper connecting element 1 has inwardly bent fixed wings, the upper connecting element 1 is capable of wrapping the vertebral body connected thereto; the upper surface of the coupling plate of the upper connecting element 1 and the lower surface of the coupling plate of the lower connecting element 3 are both provided with a small-tooth structure and can be attached to the adjacent vertebral bodies; the upper surface of the coupling plate of the upper connecting element 1 and the lower surface of the lower connecting element 3 are coated with a biological hydroxyapatite coating, so that the upper connecting element 1 and the lower connecting element 3 are respectively fused with the adjacent vertebral bodies; since the middle portion of the upper connecting element 1, of the artificial vertebral body element 2 and of the lower connecting element 3 are all provided with bone graft channels, bone to be grafted can be inserted therein, which facilitates the bone to be grown into the adjacent vertebral bodies.

Embodiment 2

In a preferred embodiment of the present invention, an assembled vertebral body comprises an upper connecting element 1, an artificial vertebral body element 2 and a lower connecting element 3.

In this embodiment, the artificial vertebral body element 2 is the same as the artificial vertebral body element 2 of Embodiment 1, and the upper connecting element 1 is different from the upper connecting element 1 of Embodiment 1, and the lower connecting element 3 is different from the lower connecting element 3 of Embodiment 1.

The difference between the upper connecting element 1 of the present embodiment and the upper connecting element 1 of Embodiment 1 is that the fixing plate of the upper connecting element 1 of this embodiment further comprises a locking device.

The difference between the lower connecting element 3 of the present embodiment and the lower connecting element 3 of Embodiment 1 is that the fixing plate of the lower connecting element 3 of this embodiment further comprises a locking device.

Figure 8A:
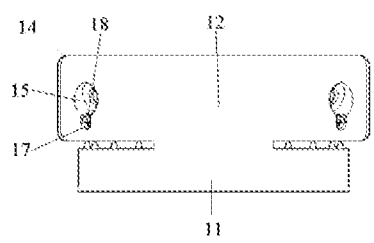
FIG. 8A is a front view of the upper connecting element of a second preferred embodiment of the present invention.
Figure 8B:
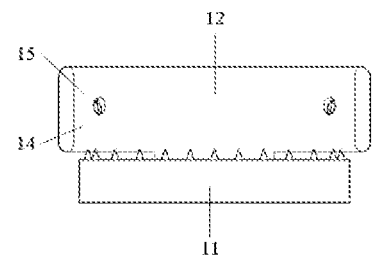
FIG. 8B is a rear view of the upper connecting element.
Figure 8C:
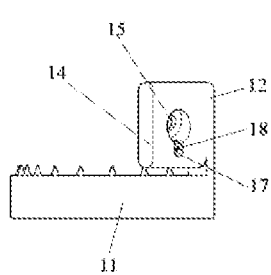
FIG. 8C is a side view of the upper connecting element.
Figure 8D:
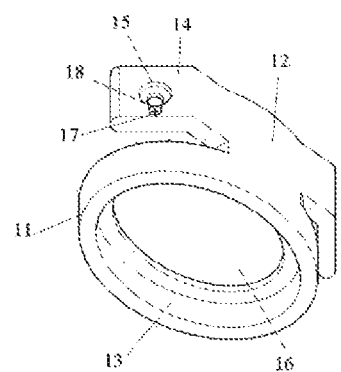
FIG. 8D is a perspective view of the upper connecting element.

As shown in FIG. 8A-8D, FIG. 8A is a front view of the upper connecting element 1; FIG. 8B is a rear view of the upper connecting element 1; and FIG. 8C is a side view of the upper connecting element 1; and FIG. 8D is a perspective view of the upper connecting element 1. The locking device is disposed outside the fixed wing 14 and is disposed around the nail hole 15, and the locking device comprises a locking slot 17 and a locking screw 18, wherein the locking slot 17 does not penetrate the fixed wing 14. The locking screw 18 is in the shape of an arch, and the arch consists of a subtense and a corresponding arc, and the angle of the arc is greater than 270° and less than 360°. In an unlocked state, the distance between the subtense edge of the locking screw 18 and a center of the nail hole 15 is less than the distance between the arc edge of the locking screw 18 and the center of the nail hole 15; in a locked state, the distance between the subtense edge of the locking screw 18 and the center of the nail hole 15 is greater than the distance between the arc edge of the locking screw 18 and the center of the nail hole 15.

Figure 9A:
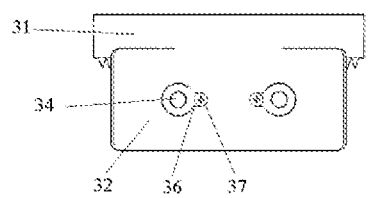
FIG. 9A is a front view of the lower connecting element of a second preferred embodiment of the present invention.
Figure 9B:
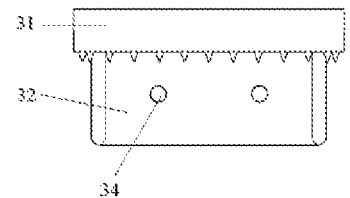
FIG. 9B is a rear view of the lower connecting element.
Figure 9C:
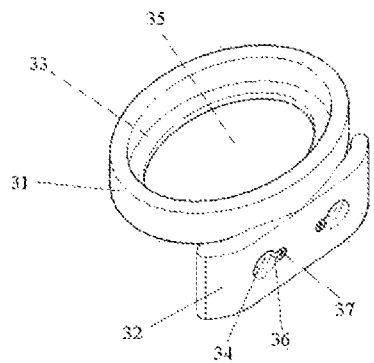
FIG. 9C is a perspective view of the lower connecting element.

As shown in FIG. 9A-9C, FIG. 9A is a front view of the lower connecting element 3; FIG. 9B is a rear view of the lower connecting element 3; and FIG. 9C is a perspective view of the lower connecting element 3. The locking device is disposed outside the fixing plate 32 and is disposed around the nail hole 34, and the locking device comprises a locking slot 36 and a locking screw 37, wherein the locking slot 37 does not penetrate the fixing plate 32. The locking screw 37 is in the shape of an arch, and the arch consists of a subtense and a corresponding arc, and the angle of the arc is greater than 270° and less than 360°. In an unlocked state, the distance between the subtense edge of the locking screw 37 and a center of the nail hole 34 is less than the distance between the arc edge of the locking screw 37 and the center of the nail hole 34; in a locked state, the distance between the subtense edge of the locking screw 37 and the center of the nail hole 34 is greater than the distance between the arc edge of the locking screw 37 and the center of the nail hole 34.

Figure 10A:
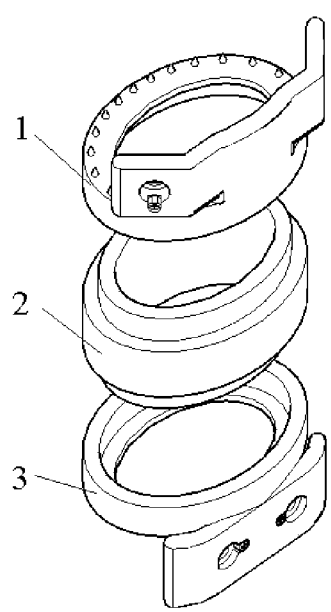
FIG. 10A is a schematic view of an assembly process in sequence of a second preferred embodiment of the present invention.
Figure 10B:
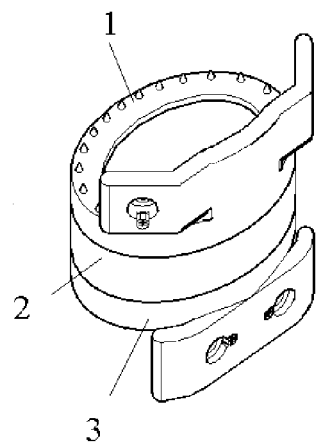
FIG. 10B is a schematic view of an assembly process in sequence of a second preferred embodiment of the present invention.
Figure 10C:
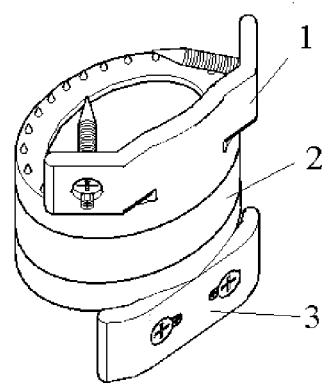
FIG. 10C is a schematic view of an assembly process in sequence of a second preferred embodiment of the present invention.

As shown in FIG. 10A-10C, the assembly process of the assembled vertebral body in this embodiment are as follows: a corresponding artificial vertebral body element 2 is designed according to the second cervical vertebrae structure of the patient and made by 3D printing; the artificial vertebral body 2 made by 3D printing is assembled to with the upper connecting element 1 and the lower connecting element 3, respectively; the assembled vertebral body is implanted into the operation site of the patient, and the upper connecting element 1 and the lower connecting element 3 are respectively fixed to the adjacent vertebral body by screws; then, the locking screw 18 of the upper connecting element 1 is rotated by 180°, and the locking screw 37 of the lower connecting element 3 is rotated by 180°, and lock the screw in the corresponding nail hole; finally, the vertebral body implantation is completed. Since the upper connecting element 1 has inwardly bent fixed wings, the upper connecting element 1 is capable of wrapping the vertebral body connected thereto; the upper surface of the coupling plate of the upper connecting element 1 and the lower surface of the coupling plate of the lower connecting element 3 are both provided with a small-tooth structure and can be attached to the adjacent vertebral bodies; the upper surface of the coupling plate of the upper connecting element 1 and the lower surface of the lower connecting element 3 are coated with a biological hydroxyapatite coating, so that the upper connecting element 1 and the lower connecting element 3 are respectively fused with the adjacent vertebral bodies; since the middle portion of the upper connecting element 1, of the artificial vertebral body element 2 and of the lower connecting element 3 are all provided with bone graft channels, bone to be grafted can be inserted therein, which facilitates the bone to be grown into the adjacent vertebral bodies; by arranging the locking device around the nail hole, implanted screws will not easily fall off, thereby improving the stability.

Embodiment 3

In a preferred embodiment of the present invention, an assembled vertebral body comprises an upper connecting element 1, an artificial vertebral body element 2 and a lower connecting element 3.

In this embodiment, the artificial vertebral body element 2 is the same as the artificial vertebral body element 2 of Embodiment 1, the lower connecting element 3 is the same as the lower connecting element 3 of Embodiment 1, and the upper connecting element 1 is different from the upper connecting element 1 of Embodiment 1.

The difference between the upper connecting element 1 of the present embodiment and the upper connecting element 1 of Embodiment 1 is that the fixing plate 12 of the upper connecting element 1 of this embodiment is straight line-shaped, and the upper connecting element 1 of the present embodiment does not have the inwardly bent fixed wing 14.

Figure 11A:
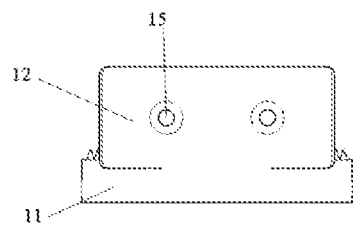
FIG. 11A is a front view of the upper connecting element of a third preferred embodiment of the present invention.
Figure 11B:
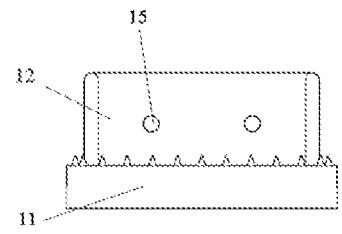
FIG. 11B is a rear view of the upper connecting element.
Figure 11C:
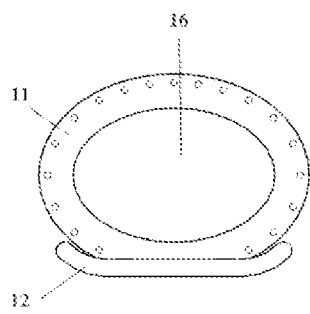
FIG. 11C is a top view of the upper connecting element.
Figure 11D:
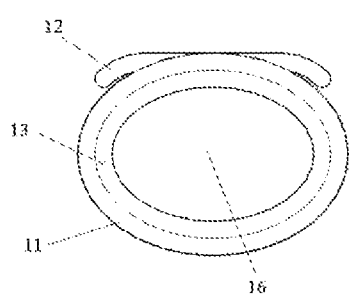
FIG. 11D is a bottom view of the upper connecting element.
Figure 11E:
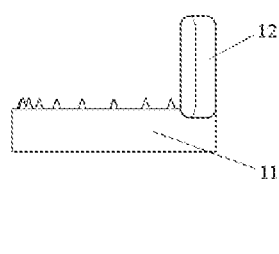
FIG. 11E is a side view of the upper connecting element.
Figure 11F:
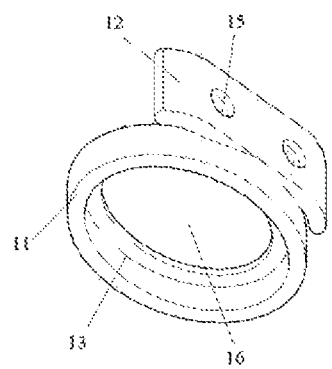
FIG. 11F is a perspective view of the upper connecting element.

As shown in FIG. 11A-11F, FIG. 11A is a front view of the upper connecting element 1; FIG. 11B is a rear view of the upper connecting element 1; FIG. 11C is a top view of the upper connecting element 1; FIG. 11D is a bottom view of the upper connecting element 1; FIG. 11E is a side view of the upper connecting element 1; and FIG. 11F is a perspective view of the upper connecting element 1. The upper connecting element 1 comprises a coupling plate 11, a fixing plate 12, and a first nesting part 13, wherein the fixing plate 12 is disposed at the upper part of the coupling plate 11, and the first nesting part 13 is disposed at the lower part of the coupling plate 11.

The coupling plate 11 has an elliptical shape, and an upper surface thereof is coated with a layer of biological hydroxyapatite coating using a plasma oxidation technique and is distributed with a small-tooth structure.

The coupling plate 11 may be a hollow structure or a solid structure.

In this embodiment, the coupling plate 11 is the hollow structure. The hollow structure is a bone graft channel 16, and the bone graft channel is disposed in a middle portion of the coupling plate 11, such that bones coming into contact with the coupling plate may grow into the bone graft channel 16.

The fixing plate 12 is arranged on one side of an upper surface of the coupling plate 11. The fixing plate 12 is straight line-shaped. As shown in FIG. 11A, the upper connecting element 1 is ⊥-shaped. As shown in FIG. 11E, the upper connecting element 1 is L-shaped.

Two through nail holes 15 are symmetrically and horizontally disposed on a left and a right side of the fixing plate 12.

The upper connecting element 1 of the present embodiment has following various embodiments:

Embodiment 1, as shown in FIG. 12A, the first nesting part 13 of the upper connecting element 1 is a protruding block, and the first nesting part 13 is elliptical;

Embodiment 2, as shown in FIG. 12B, the first nesting part 13 of the upper connecting element 1 is a recessed groove, and the first nesting part 13 has a rounded rectangle shape;

Embodiment 3, as shown in FIG. 12C, the first nesting part 13 of the upper connecting element 1 is a protruding block, and the first nesting part 13 has a rounded rectangle shape. In addition, the coupling plate 11 is a solid structure without the bone graft channel 16.

Figure 13A:
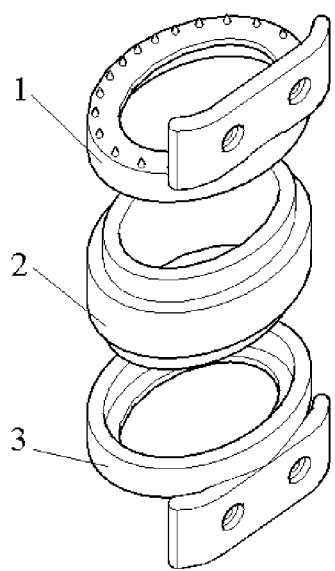
FIG. 13A is a schematic view of an assembly process in sequence of a third preferred embodiment of the present invention.
Figure 13B:
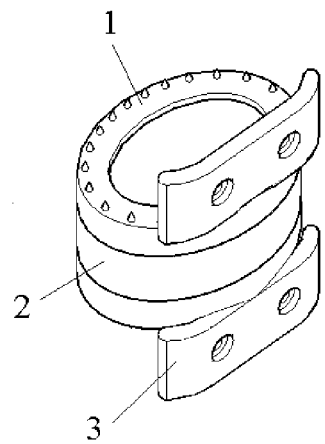
FIG. 13B is a schematic view of an assembly process in sequence of a third preferred embodiment of the present invention.
Figure 13C:
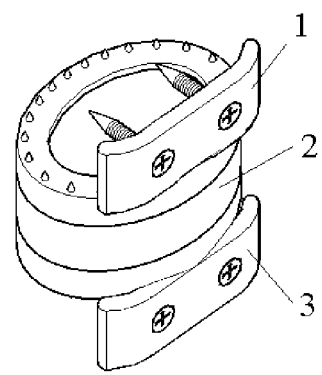
FIG. 13C is a schematic view of an assembly process in sequence of a third preferred embodiment of the present invention.

As shown in FIG. 13A-13C, the assembly process of the assembled vertebral body in this embodiment are as follows: a corresponding artificial vertebral body element 2 is designed according to the second cervical vertebrae structure of the patient and made by 3D printing; the artificial vertebral body 2 made by 3D printing is assembled with the upper connecting element 1 and the lower connecting element 3, respectively; the assembled vertebral body is implanted into the operation site of the patient, and the upper connecting element 1 and the lower connecting element 3 are respectively fixed to the adjacent vertebral body by screws, finally, the vertebral body implantation is completed. The upper surface of the coupling plate of the upper connecting element 1 and the lower surface of the coupling plate of the lower connecting element 3 are both provided with a small-tooth structure and can be attached to the adjacent vertebral bodies; the upper surface of the coupling plate of the upper connecting element 1 and the lower surface of the lower connecting element 3 are coated with a biological hydroxyapatite coating, so that the upper connecting element 1 and the lower connecting element 3 are respectively fused with the adjacent vertebral bodies; since the middle portion of the upper connecting element 1, of the artificial vertebral body element 2 and of the lower connecting element 3 are all provided with bone graft channels, bone to be grafted can be inserted therein, which facilitates the bone to be grown into the adjacent vertebral bodies.

Embodiment 4

In a preferred embodiment of the present invention, an assembled vertebral body comprises an upper connecting element 1, an artificial vertebral body element 2 and a lower connecting element 3.

In this embodiment, the artificial vertebral body element 2 is the same as the artificial vertebral body element 2 of Embodiment 2, the lower connecting element 3 is the same as the lower connecting element 3 of Embodiment 2, and the upper connecting element 1 is different from the upper connecting element 1 of Embodiment 2.

The difference between the upper connecting element 1 of the present embodiment and the upper connecting element 1 of Embodiment 3 is that the fixing plate 12 of the upper connecting element 1 of this embodiment is straight line-shaped, and the upper connecting element 1 of the present embodiment does not have the inwardly bent fixed wing 14.

As shown in FIG. 14A-14C, FIG. 14A is a front view of the upper connecting element 1; FIG. 14B is a rear view of the upper connecting element 1; FIG. 14C is a perspective view of the upper connecting element 1. The upper connecting element 1 comprises a coupling plate 11, a fixing plate 12, and a first nesting part 13, wherein the fixing plate 12 is disposed at the upper part of the coupling plate 11, and the first nesting part 13 is disposed at the lower part of the coupling plate 11.

The coupling plate 11 has an elliptical shape, and an upper surface thereof is coated with a layer of biological hydroxyapatite coating using a plasma oxidation technique and is distributed with a small-tooth structure.

The coupling plate 11 may be a hollow structure or a solid structure.

In this embodiment, the coupling plate 11 is the hollow structure. The hollow structure is a bone graft channel 16, and the bone graft channel is disposed in a middle portion of the coupling plate 11, such that bones coming into contact with the coupling plate may grow into the bone graft channel 16.

The fixing plate 12 is arranged on one side of an upper surface of the coupling plate 11. The fixing plate 12 is straight line-shaped. As shown in FIG. 11A, the upper connecting element 1 is ⊥-shaped. As shown in FIG. 11E, the upper connecting element 1 is L-shaped.

Two nail holes 15 are symmetrically and horizontally disposed on a left and a right side of the fixing plate 12.

Figure 15A:
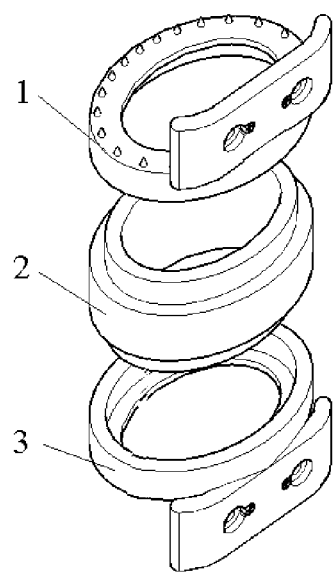
FIG. 15A is a schematic view of an assembly process in sequence of a fourth preferred embodiment of the present invention.
Figure 15B:
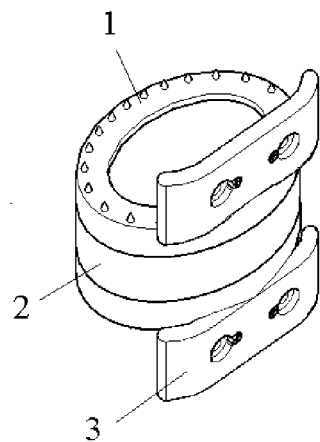
FIG. 15B is a schematic view of an assembly process in sequence of a fourth preferred embodiment of the present invention.
Figure 15C:
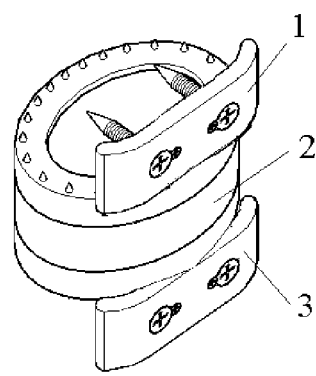
FIG. 15C is a schematic view of an assembly process in sequence of a fourth preferred embodiment of the present invention.

As shown in FIG. 15A-15C, the assembly process of the assembled vertebral body in this embodiment are as follows: a corresponding artificial vertebral body element 2 is designed according to the second cervical vertebrae structure of the patient and made by 3D printing; the artificial vertebral body 2 made by 3D printing is assembled with the upper connecting element 1 and the lower connecting element 3, respectively; the assembled vertebral body is implanted into the operation site of the patient, and the upper connecting element 1 and the lower connecting element 3 are respectively fixed to the adjacent vertebral body by screws; then, the locking screw 18 of the upper connecting element 1 is rotated by 180°, and the locking screw 37 of the lower connecting element 3 is rotated by 180°, and lock the screw in the corresponding nail hole; finally, the vertebral body implantation is completed. Since the upper connecting element 1 has inwardly bent fixed wings, the upper connecting element 1 is capable of wrapping the vertebral body connected thereto; the upper surface of the coupling plate of the upper connecting element 1 and the lower surface of the coupling plate of the lower connecting element 3 are both provided with a small-tooth structure and can be attached to the adjacent vertebral bodies; the upper surface of the coupling plate of the upper connecting element 1 and the lower surface of the lower connecting element 3 are coated with a biological hydroxyapatite coating, so that the upper connecting element 1 and the lower connecting element 3 are respectively fused with the adjacent vertebral bodies; since the middle portion of the upper connecting element 1, of the artificial vertebral body element 2 and of the lower connecting element 3 are all provided with bone graft channels, bone to be grafted can be inserted therein, which facilitates the bone to grown into the adjacent vertebral bodies; by arranging the locking device around the nail hole, implanted screws will not easily fall off, thereby improving the stability.

Embodiment 5

In a preferred embodiment of the present invention, an assembled vertebral body comprises an upper connecting element 1, an artificial vertebral body element 2 and a lower connecting element 3.

Figure 16A:
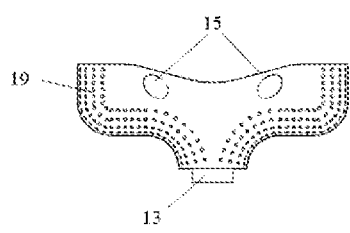
FIG. 16A is a front view of the upper connecting element of a fifth preferred embodiment of the present invention.
Figure 16B:
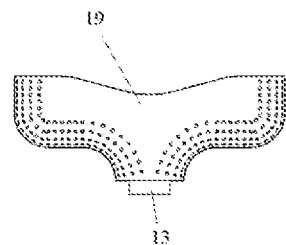
FIG. 16B is a rear view of the upper connecting element.
Figure 16C:
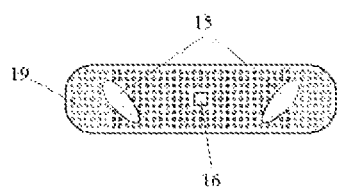
FIG. 16C is a top view of the upper connecting element.
Figure 16D:
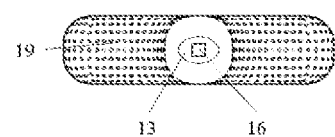
FIG. 16D is a bottom view of the upper connecting element.
Figure 16E:
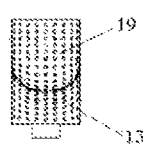
FIG. 16E is a side view of the upper connecting element.
Figure 16F:
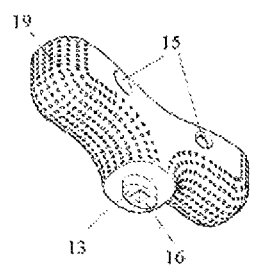
FIG. 16F is a perspective view of the upper connecting element.

As shown in FIG. 16A-16F, FIG. 16A is a front view of the upper connecting element 1; FIG. 16B is a rear view of the upper connecting element 1; FIG. 16C is a top view of the upper connecting element 1; FIG. 16D is a bottom view of the upper connecting element 1; FIG. 16E is a side view of the upper connecting element 1; and FIG. 16F is a perspective view of the upper connecting element 1. The upper connecting element 1 comprises a transverse portion 19 and a first nesting part 13, wherein the first nesting part 13 is disposed at a lower part of the transverse portion 19.

The transverse portion 19 comprises two nail holes 15 symmetrically disposed on a left and a right side of a front end surface of the transverse portion 19, and the nail holes 15 penetrate the front end surface of the transverse portion 19 and an upper end surface of the transverse portion 19.

The transverse portion 19 is V-shaped or has a shape of a semi-concave sphere, and a left and a right end of the transverse portion 19 project upwards, and the assembled vertebral body is Y-shaped.

A front end surface and/or a rear end surface of the transverse portion 19 is a polished structure, and the rest of surfaces are distributed with the spongy microporous structure.

The front surface of the transverse portion 19 is a matte surface.

The transverse portion 19 may be a hollow structure or a solid structure.

In this embodiment, the transverse portion 19 is a hollow structure. The hollow structure is a bone graft channel 16, and the bone graft channel 16 is disposed in a middle portion of the transverse portion 19, that is, penetrating through the upper end surface and the lower end surface of the transverse portion 19.

The first nesting part 13 is a protruding block, and the first nesting part 13 is elliptical.

Figure 17C:
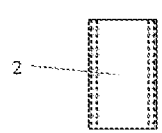
FIG. 17C is a perspective view of the artificial vertebral body element.
Figure 17C:
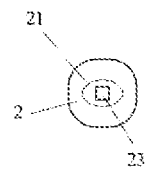
Figure 17C:
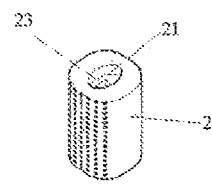

As shown in FIG. 17A-17C, FIG. 17A is a front view of the artificial vertebral body element 2; FIG. 17B is a top view (bottom view) of the artificial vertebral body element 2; and FIG. 17C is a perspective view of the artificial vertebral body element 2. The artificial vertebral body element 2 comprises a third nesting part 21 and a fourth nesting part 22, wherein both the third nesting part 21 and the fourth nesting part 22 are recessed grooves, and the artificial vertebral body element 2 is H-shaped.

The artificial vertebral body element 2 may be a hollow structure or a solid structure.

In this embodiment, the artificial vertebral body element 2 is a hollow structure. The hollow structure is a bone graft channel 23, and the bone graft channel 23 is disposed in a middle portion of the artificial vertebral body element 2, that is, penetrating through the upper end surface and the lower end surface of the artificial vertebral body element 2.

A front end surface and/or a rear end surface of the artificial vertebral body element 2 is a polished structure, and the rest of surfaces are distributed with the spongy microporous structure.

The third nesting part 21 and the fourth nesting part 22 are elliptic.

As shown in FIG. 18A-18F, FIG. 18A is a front view of the lower connecting element 3; FIG. 18B is a rear view of the lower connecting element 3; FIG. 18C is a top view of the lower connecting element 3; FIG. 18D is a bottom view of the lower connecting element 3; FIG. 18E is a side view of the lower connecting element 3; and FIG. 18F is a perspective view of the lower connecting element 3. The lower connecting element 3 comprises a transition portion 38, a mating portion 39 and a second nesting part 33, wherein, the second nesting part 33 is disposed at an upper portion of the transition portion 38, and the mating portion 33 is disposed at a lower portion of the transition portion 38.

The mating portion 39 is provided on the outside of the lower portion of the transition portion 38 and transits smoothly.

The mating portion 39 comprises nail holes 34 symmetrically and horizontally arranged at a front end surface of the mating portion 39 and penetrating the front end surface and a rear end surface of the mating portion 39.

A front end surface and/or a rear end surface of the transition portion 38 is a polished structure, and the rest of surfaces are distributed with the spongy microporous structure.

The lower surface of the transition portion 38 is a matte surface.

The transition portion 38 may be a hollow structure or a solid structure.

In this embodiment, the transition portion 38 is the hollow structure. The hollow structure is a bone graft channel 35, and the bone graft channel 35 is disposed in a middle portion of the transition portion 38, that is, penetrating through the upper end surface and the lower end surface of the transition portion 38.

The second nesting part 33 is a protruding block, and the second nesting part 13 is elliptical.

A size of the transition portion 38 is equal to the size of the artificial vertebral body element 2.

A length of the mating portion 39 is equal to the length of 1 to 2 cervical spines, preferably the length of one cervical spine.

A width of the mating portion 39 is greater than the width of the transition portion 38.

The width of the transition portion 38 is from 10 mm to 16 mm, and the width of the mating portion 39 is from 12 mm to 22 mm.

The upper connecting element 1, the artificial vertebral body element 2 and the lower connecting element 3 are all made of a titanium alloy material.

The lower connecting element 3 is a standard part, while the upper connecting element 1 and the artificial vertebral body element 2 are non-standard parts. The term "standard part" means that lower connecting element 3 can be mass-produced and need not to be redesigned according to patient's health condition. The term "non-standard part" means that the upper connecting element 1 and the artificial vertebral body element 2 need to be designed according to the patient's health condition and made by 3D printing. Specifically, the length of the artificial vertebral body element 2 needs to be designed.

In this embodiment, the upper connecting element 1, the artificial vertebral body element 2 and the lower connecting element 3 of the present embodiment have other embodiments.

The upper connecting element 1 of the present embodiment has following various embodiments:

Embodiment 1, as shown in FIG. 19A, the first nesting part 13 of the upper connecting element 1 is a recessed groove, and the first nesting part 13 is elliptical;

Embodiment 2, as shown in FIG. 19B, the transverse portion 19 of the upper connecting element 1 is straight line-shaped, all the surfaces of the transverse portion 19 are polished structures, and the transverse portion 19 is a solid structure. The first nesting part 13 is a protruding block, and the first nesting part 13 is elliptic, and the assembled vertebral body is T-shaped;

Embodiment 3, as shown in FIG. 19C, the transverse portion 19 of the upper connecting element 1 is inversed V-shaped or has a shape of a semi-convex sphere, and two ends of the transverse portion 19 project downwards. In addition, the surfaces of the transverse portion 19 are distributed with the spongy microporous structure. The first nesting part 13 is a protruding block, and the assembled vertebral body is t-shaped;

Embodiment 4, as shown in FIG. 19D, the transverse portion of the upper connecting element 1 is W-shaped. The left end, the right end and a central portion of the transverse portion 19 project upward, and the surfaces of the transverse portion 19 are distributed with the spongy microporous structure. The first nesting part 13 is a protruding block.

Figure 20A:
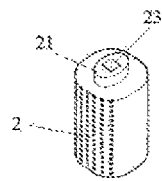
FIG. 20A is a perspective view of a first alternative embodiment of the artificial vertebral body element of the fifth preferred embodiment of the present invention observed from the top.
Figure 20B:
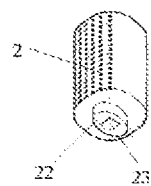
FIG. 20B is a perspective view of the first alternative embodiment of the artificial vertebral body element observed from the bottom.
Figure 20C:
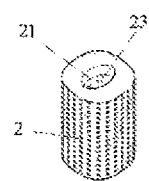
FIG. 20C is a perspective view of a second alternative embodiment of the artificial vertebral body element observed from the top.
Figure 20D:
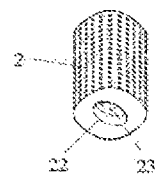
FIG. 20D is a perspective view of the second alternative embodiment of the artificial vertebral body element observed from the bottom.
Figure 20E:
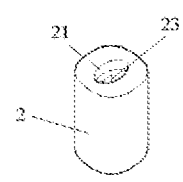
FIG. 20E is a perspective view of a third alternative embodiment of the artificial vertebral body element of the first preferred embodiment observed from the top.
Figure 20F:
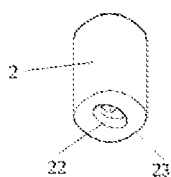
FIG. 20F is a perspective view of the third alternative embodiment of the artificial vertebral body element observed from the bottom.

The artificial vertebral body element 2 of the present embodiment has following various embodiments:

Embodiment 1, as shown in FIG. 20A-20B, FIG. 20A is a perspective view of the artificial vertebral body element 2 observed from the top; FIG. 20B is a perspective view of the artificial vertebral body element 2 observed from the bottom. Both the third nesting part 21 and the fourth nesting part 22 of the artificial vertebral body element 2 are protruding blocks; the artificial vertebral body element 2 is cross-shaped, and both the third nesting part 21 and the fourth nesting part 22 are elliptic; a front end surface and/or a rear end surface of the artificial vertebral body element 2 is a polished structure, and the rest of surfaces are distributed with the spongy microporous structure;

Embodiment 2, as shown in FIG. 20C-20D, FIG. 20C is a perspective view of the artificial vertebral body element 2 observed from the top; FIG. 20D is a perspective view of the artificial vertebral body element 2 observed from the bottom. Both the third nesting part 21 and the fourth nesting part 22 of the artificial vertebral body element 2 are recessed grooves; the artificial vertebral body element 2 is H-shaped, and both the third nesting part 21 and the fourth nesting part 22 are elliptic; and the surfaces of the artificial vertebral body element 2 are distributed with the spongy microporous structure;

Embodiment 3, as shown in FIG. 20E-20F, FIG. 20E is a perspective view of the artificial vertebral body element 2 observed from the top; FIG. 20F is a perspective view of the artificial vertebral body element 2 observed from the bottom. Both the third nesting part 21 and the fourth nesting part 22 of the artificial vertebral body element 2 are recessed grooves; the artificial vertebral body element 2 is H-shaped, and both the third nesting part 21 and the fourth nesting part 22 are elliptic; and all the surfaces of the artificial vertebral body element 2 are polished structures.

The lower connecting element 3 of the present embodiment has following various embodiments:

Embodiment 1, as shown in FIG. 21A, the second nesting part 33 of the lower connecting element 3 is a recessed groove, and the second nesting part 33 is elliptical;

Embodiment 2, as shown in FIG. 21B, the second nesting part 33 of the lower connecting element 3 is a protruding block, and the second nesting part 33 is elliptical. All the surfaces of the transition portion 38 of the lower connecting element 3 are polished structures;

Embodiment 3, as shown in FIG. 21C, the second nesting part 33 of the lower connecting element 3 is a protruding block, and the second nesting part 33 is elliptical. The surfaces of the transition portion 38 of the lower connecting element 3 are distributed with the spongy microporous structure;

Embodiment 4, as shown in FIG. 21D, the second nesting part 33 of the lower connecting element 3 is a protruding block, the second nesting part 33 is elliptical, and all the surfaces of the transition portion 38 of the lower connecting member 3 are polished structures. The nail hole 34 is symmetrically and vertically disposed on the front end surface of the mating portion 39, and the nail hole 34 penetrates the front end surface of the mating portion 39 and the rear end surface of the mating portion 39;

Embodiment 5, as shown in FIG. 21E, the second nesting part 33 of the lower connecting element 3 is a protruding block, the second nesting part 33 is elliptical, and all the surfaces of the transition portion 38 of the lower connecting element 3 are polished structures. The nail hole 34 is disposed on the front end surface of the mating portion 39 in an inverted triangle shape, and the nail hole 34 penetrates the front end surface of the mating portion 39 and the rear end surface of the mating portion 39;

Embodiment 6, as shown in FIG. 21F, the second nesting part 33 of the lower connecting element 3 is a protruding block, the second nesting part 33 is elliptical, and all the surfaces of the transition portion 38 of the lower connecting element 3 are polished structures. The mating portion 39 is arranged inside the lower portion of the transition portion 38. The front end surface of the connection portion between the mating portion 39 and the transition portion 38 is a flat surface.

Figure 22A:
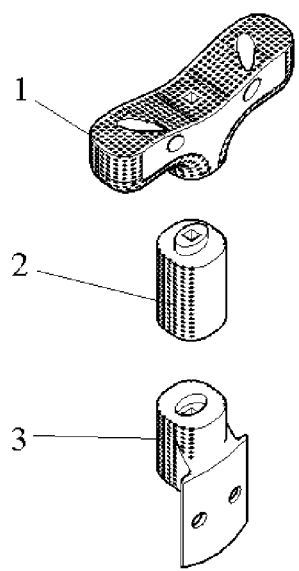
FIG. 22A is a schematic view of an assembly process in sequence of the fifth preferred embodiment of the present invention.
Figure 22B:
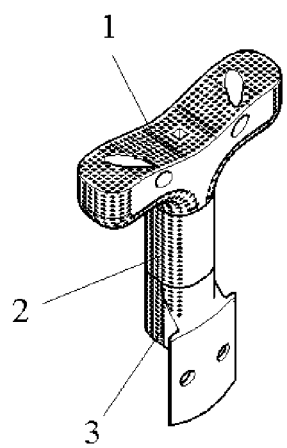
FIG. 22B is a schematic view of an assembly process in sequence of the fifth preferred embodiment of the present invention.
Figure 22C:
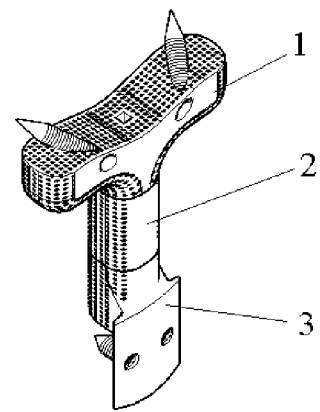
FIG. 22C is a schematic view of an assembly process in sequence of the fifth preferred embodiment of the present invention.

As shown in FIG. 22A-22C, the assembly process of the assembled vertebral body in this embodiment are as follows: a corresponding upper connecting element 1 and an artificial vertebral body element 2 are designed according to the second cervical vertebrae structure of the patient and made by 3D printing; the artificial vertebral body 2 made by 3D printing is assembled with the upper connecting element 1 and the lower connecting element 3, respectively; the assembled vertebral body is implanted into the operation site of the patient, and the upper connecting element 1 and the lower connecting element 3 are respectively fixed to the adjacent vertebral body by screws, finally, the vertebral body implantation is completed. By using the oblique upward nail hole 15, the assembled vertebral body can be directly set below the atlas, and implements a bearing-type fixing instead of the traditional encircling fixing, so that the upper end of the transverse portion 19 is in contact with the bottom of the atlas, increasing the contact area between the transverse portion 19 of the atlas and the anterior arch of the atlas or the skull base to form an effective support, which is conducive to bone ingrowth; the transverse portion 19 is fixed by means of a bearing, and screws are positioned on the massa lateralis atlantis or condylus occipitalis from an area below the upper contact area to the area above the two sides, such that the prosthesis can perform occipito-cervical reconstruction after the atlantoaxial resection. The mating portion 39 adopts a cross-fixation system using vertebral body screws and end plate screws, thereby having a good pull-out resistance and anti-rotation ability.

The above descriptions are only the preferred embodiments of the invention, not thus limiting the embodiments and scope of the invention. Those skilled in the art should be able to realize that the schemes obtained from the content of specification and drawings of the invention are within the scope of the invention.

What is claimed is:

1. An assembled vertebral body used in a cervical reconstruction operation, comprising: an upper connecting element, an artificial vertebral body element and a lower connecting element, wherein the upper connecting element is disposed at an upper part of the artificial vertebral body element, wherein the lower connecting element is disposed at a lower part of the artificial vertebral body element, wherein the artificial vertebral body element is nestedly connected with the upper connecting element and the lower connecting element, respectively, wherein the upper connecting element comprises a first nesting part disposed at a lower part of the upper connecting element, wherein the lower connecting element comprises a second nesting part disposed at an upper part of the lower connecting element, wherein the artificial vertebral body element comprises a third nesting part disposed at the upper part of the artificial vertebral body element and a fourth nesting part disposed at the lower part of the artificial vertebral body element, wherein the first nesting part is nestedly connected with the third nesting part, wherein the second nesting part is nestedly connected with the fourth nesting part, wherein a nest connection in between the first nesting part and the third nesting part is an anti-axial rotation nested connection, wherein a nest connection in between the second nesting part and the fourth nesting part is an anti-axial rotation nested connection, wherein the first nesting part, the second nesting part, the third nesting part and the fourth nesting part have a non-circular shape, wherein the non-circular shape is an ellipse or a rounded rectangle, wherein the upper connecting element further comprises a coupling plate and a fixing plate, wherein the fixing plate of the upper connecting element is disposed at an upper part of the coupling plate of the upper connecting element, wherein the first nesting part is disposed at a lower part of the coupling plate of the upper connecting element, wherein the lower connecting element further comprises a coupling plate and a fixing plate, wherein the fixing plate of the lower connecting element is disposed at a lower part of the coupling plate of the lower connecting element, wherein the second nesting part is disposed at an upper part of the coupling plate of the lower connecting element, wherein the upper connecting element further comprises a transverse portion, wherein the first nesting part is disposed at a lower part of the transverse portion, wherein the lower connecting element further comprises a transition portion and a mating portion, wherein the mating portion is disposed at a lower portion of the transition portion, wherein the second nesting part is disposed at an upper portion of the transition portion, a front end surface and/or a rear end surface of the transition portion is a polished structure, and the rest of the surfaces of the transition portion are distributed with a spongy microporous structure, the lower surface of the transition portion is a matte surface, the transition portion is a hollow structure, the hollow structure is a bone graft channel, a size of the transition portion is equal to a size of the artificial vertebral body element, a length of the mating portion is equal to a length of 1 to 2 cervical spines, a width of the mating portion is greater than the width of the transition portion.

2. The assembled vertebral body of claim 1, wherein the first nesting part and the second nesting part are protruding blocks, the third nesting part and the fourth nesting part are recessed grooves; or the first nesting part and the fourth nesting part are protruding insert blocks, and the second nesting part and the third nesting part are recessed grooves; or the first nesting part and the fourth nesting part are recessed grooves, and the second nesting part and the third nesting part are protruding blocks; or the first nesting part and the second nesting part are recessed grooves, and the third nesting part and the fourth nesting part are protruding blocks.

3. The assembled vertebral body of claim 1, wherein the fixing plate of the upper connecting element and the fixing plate of the lower connecting element are both T-shaped.

4. The assembled vertebral body of claim 3, wherein two fixing wings, bent inward at a certain angle, are provided at a left and a right side of the fixing plate, respectively.

5. The assembled vertebral body of claim 4, wherein the fixing plate comprises nail holes symmetrically disposed throughout the fixed wings on both sides of the fixing plate.

6. The assembled vertebral body of claim 5, wherein the nail holes penetrate upwardly from an outer side of the fixed wing to an inner side of the fixed wing at an angle with respect to a horizontal plane.

7. The assembled vertebral body of claim 5, wherein the upper connecting element comprises a locking device disposed around the nail hole.

8. The assembled vertebral body of claim 7, wherein the locking device comprises a locking slot disposed on one side of the nail hole and a locking screw disposed within the locking slot.

9. The assembled vertebral body of claim 1, wherein the fixing plate of the upper connecting element and the fixing plate of the lower connecting element each have a cross sectional shape in the form of a straight line.

10. The assembled vertebral body of claim 9, wherein the fixing plate comprises nail holes symmetrically disposed throughout a left side and a right side of the fixing plate.

11. The assembled vertebral body of claim 10, wherein the lower connecting element comprises a locking device disposed around the nail hole.

12. The assembled vertebral body of claim 11, wherein the locking device comprises a locking slot disposed on one side of the nail hole and a locking screw disposed within the locking slot.

13. The assembled vertebral body of claim 1, wherein the transverse portion comprises nail holes symmetrically disposed on a left and a right side of a front end surface of the transverse portion, and the nail holes penetrate the front end surface of the transverse portion and an upper end surface of the transverse portion.

14. The assembled vertebral body of claim 13, wherein the transverse portion has a cross sectional shape in the form of a straight line; or the transverse portion is V-shaped or has a shape of a semi-concave sphere, and a left and a right end of the transverse portion project upwards; or the transverse portion is inverted V-shaped or has the shape of a semi-convex sphere, and the left and the right end of the transverse portion project downwards; or the transverse portion is W-shaped, and the left end, the right end and a central portion of the transverse portion project upwards.

15. The assembled vertebral body of claim 1, wherein the mating portion comprises nail holes penetrating a front end surface and a rear end surface of the mating portion.

16. The assembled vertebral body of claim 15, wherein the nail holes are symmetrically and horizontally arranged; or the nail holes are symmetrically and vertically arranged; or the nail holes are symmetrically arranged in a triangle.

17. The assembled vertebral body of claim 1, wherein an upper surface of the upper connecting element and/or a lower surface of the lower connecting element are/is provided with a small-tooth structure.

18. The assembled vertebral body of claim 1, wherein the upper surface of the upper connecting element and/or the lower surface of the lower connecting element are/is provided with a biological hydroxyapatite coating.

* * * * *